US007865374B2

(12) United States Patent
Ash et al.

(10) Patent No.: US 7,865,374 B2
(45) Date of Patent: Jan. 4, 2011

(54) COMPUTERIZED SYSTEM AND METHOD FOR VERIFYING AUTHORITY TO MODIFY CLINICAL ORDERS

(75) Inventors: Michael A. Ash, Parkville, MO (US); John Q. DeVerter, Liberty, MO (US)

(73) Assignee: Cerner Innovation, Inc., Kansas City, MO (US)

( * ) Notice: Subject to any disclaimer, the term of this patent is extended or adjusted under 35 U.S.C. 154(b) by 886 days.

(21) Appl. No.: 11/359,011

(22) Filed: Feb. 22, 2006

(65) Prior Publication Data
US 2007/0198292 A1 Aug. 23, 2007

(51) Int. Cl.
G06Q 10/00 (2006.01)
G06Q 50/00 (2006.01)
A61B 5/00 (2006.01)
G06F 19/00 (2006.01)

(52) U.S. Cl. ............................................. 705/2; 705/3
(58) Field of Classification Search .................... 705/2, 705/3
See application file for complete search history.

(56) References Cited

U.S. PATENT DOCUMENTS

| 4,847,764 | A | | 7/1989 | Halvorson |
| 5,740,800 | A | | 4/1998 | Hendrickson et al. |
| 5,758,095 | A | | 5/1998 | Albaum et al. |
| 5,781,442 | A | * | 7/1998 | Engleson et al. ............ 700/214 |
| 5,826,237 | A | | 10/1998 | Macrae et al. |
| 5,845,255 | A | | 12/1998 | Mayaud |
| 5,912,818 | A | * | 6/1999 | McGrady et al. ............ 700/232 |
| 5,946,659 | A | | 8/1999 | Lancelot et al. |
| 6,031,621 | A | * | 2/2000 | Binder ........................ 358/1.1 |
| 6,061,657 | A | * | 5/2000 | Whiting-O'Keefe ........... 705/2 |
| 6,493,427 | B1 | | 12/2002 | Kobylevsky et al. |
| 6,611,846 | B1 | | 8/2003 | Stoodley |
| 2001/0050610 | A1 | * | 12/2001 | Gelston .................... 340/5.53 |
| 2002/0038392 | A1 | * | 3/2002 | De La Huerga ................ 710/8 |
| 2002/0082480 | A1 | * | 6/2002 | Riff et al. ................... 600/300 |
| 2002/0184055 | A1 | | 12/2002 | Naghavi et al. |

(Continued)

OTHER PUBLICATIONS

USPTO Office Action of May 11, 2010- U.S. Appl. No. 11/021,509, filed Dec. 22, 2004.

(Continued)

*Primary Examiner*—Gerald J. O'Connor
*Assistant Examiner*—Amber Altschul
(74) *Attorney, Agent, or Firm*—Shook, Hardy & Bacon LLP

(57) ABSTRACT

Computerized methods for verifying authority to modify clinical orders are provided. The methods may include receiving a clinical order having components associated with a plurality of phases; associating a plurality of the components to form a cross-phase group, the components including components associated with a first phase and a second phase, each of the components including a common attribute; receiving an indication to modify the common attribute of the component associated with the first phase; and determining whether a user from whom the indication is received has the authority to modify the common attribute. If it is determined that the user has the authority, the method may further include modifying all components that are associated in the group. If it is determined that the user does not have the authority, the method may further include not modifying the common attribute. Computerized systems for performing the disclosed methods are also provided.

16 Claims, 18 Drawing Sheets

U.S. PATENT DOCUMENTS

| | | | |
|---|---|---|---|
| 2003/0050801 | A1 | 3/2003 | Ries et al. |
| 2003/0144874 | A1 | 7/2003 | Barret et al. |
| 2003/0144886 | A1 | 7/2003 | Taira |
| 2003/0212577 | A1 | 11/2003 | Nichtberger |
| 2003/0236683 | A1 | 12/2003 | Henderson et al. |
| 2004/0034550 | A1 | 2/2004 | Menschik et al. |
| 2004/0153341 | A1 | 8/2004 | Brandt et al. |
| 2004/0172301 | A1 | 9/2004 | Mihai et al. |
| 2004/0267575 | A1 | 12/2004 | Boing |
| 2005/0015279 | A1 | 1/2005 | Rucker |
| 2006/0136268 | A1 | 6/2006 | Ash et al. |

OTHER PUBLICATIONS

USPTO Office Action of Apr. 27, 2010- U.S. Appl. No. 11/021,531, filed Dec. 22, 2004.

Non Final Office Action of U.S. Appl. No. 11/359,012, mailed May 25, 2010.

Non Final Office Action of U.S. Appl. No. 11/020,489, mailed May 12, 2010.

USPTO Office Action of Dec. 22, 2008—U.S. Appl. No. 11/021,509, filed Dec. 22, 2004.

USPTO Office Action of Mar. 16, 2009—U.S. Appl. No. 11/022,540, filed Dec. 22, 2004.

USPTO Office Action of Oct. 30, 2008—U.S. Appl. No. 11/022,540, filed Dec. 22, 2004.

USPTO Office Action of Sep. 2, 2009—U.S. Appl. No. 11/021,509, filed Dec. 22, 2004.

USPTO Office Action of Apr. 28, 2009- U.S. Appl. No. 11/021,531, filed Dec. 22, 2004.

USPTO Office Action of Oct. 15, 2008- U.S. Appl. No. 11/021,531, filed Dec. 22, 2004.

USPTO Office Action of Jun. 4, 2009- U.S. Appl. No. 11/020,489, filed Dec. 22, 2004.

USPTO Office Action of Aug. 31, 2009- U.S. Appl. No. 11/021,509, filed Dec. 22, 2004.

USPTO Office Action of Apr. 21, 2008—U.S. Appl. No. 11/022,540, filed Dec. 22, 2004.

USPTO Office Action of May 26, 2009- U.S. Appl. No. 11/359,013, filed Dec. 22, 2006.

USPTO Office Action of Nov. 24, 2009- U.S. Appl. No. 11/359,013, filed Dec. 22, 2006.

USPTO Office Action of Nov. 30, 2009—U.S. Appl. No. 11/022,540, filed Dec. 22, 2004.

USPTO Office Action of Jan. 7, 2010- U.S. Appl. No. 11/020,489, filed Dec. 22, 2004.

\* cited by examiner

ns disclosed in the commonly assigned application U.S. application Ser. No. 11/022,540, filed on Dec. 22, 2004, entitled "System and Method for Maintaining the Association of Healthcare Orders in a Healthcare Plan in a Computerized Pharmacy Application", U.S. application Ser. No. 11/020, 489, filed on Dec. 22, 2004, entitled "System and Method for Associating Healthcare Orders in a Healthcare Plan in a Computerized Environment", U.S. application Ser. No. 11/021, 509, filed on Dec. 22, 2004, entitled "System and Method for Maintaining the Association of Healthcare Orders from a Healthcare Plan in a Computerized Medical Administration Record", and U.S. application Ser. No. 11/021,531, filed on Dec. 22, 2004, entitled "System and Method for Creating and Maintaining Dynamic Offset Times for Healthcare Orders in a Computerized Environment", each of which is incorporated by reference herein. This application is further related by subject matter to the inventions disclosed in the commonly assigned application U.S. application Ser. No. 11/359,013, entitled "Computerized System and Method for Breaking-Out and Modifying Components of Cross-Phase Groups", and U.S. application Ser. No. 11/359,012, entitled "Computerized System and Method for Modifying Components of Healthcare Orders Which Are Associated Into Cross-Phase Groups", each of which was filed on even date herewith.

COMPUTERIZED SYSTEM AND METHOD FOR VERIFYING AUTHORITY TO MODIFY CLINICAL ORDERS

CROSS-REFERENCE TO RELATED APPLICATIONS

This application is related by subject matter to the inventions disclosed in the commonly assigned application U.S. application Ser. No. 11/022,540, filed on Dec. 22, 2004, entitled "System and Method for Maintaining the Association of Healthcare Orders in a Healthcare Plan in a Computerized Pharmacy Application", U.S. application Ser. No. 11/020, 489, filed on Dec. 22, 2004, entitled "System and Method for Associating Healthcare Orders in a Healthcare Plan in a Computerized Environment", U.S. application Ser. No. 11/021, 509, filed on Dec. 22, 2004, entitled "System and Method for Maintaining the Association of Healthcare Orders from a Healthcare Plan in a Computerized Medical Administration Record", and U.S. application Ser. No. 11/021,531, filed on Dec. 22, 2004, entitled "System and Method for Creating and Maintaining Dynamic Offset Times for Healthcare Orders in a Computerized Environment", each of which is incorporated by reference herein. This application is further related by subject matter to the inventions disclosed in the commonly assigned application U.S. application Ser. No. 11/359,013, entitled "Computerized System and Method for Breaking-Out and Modifying Components of Cross-Phase Groups", and U.S. application Ser. No. 11/359,012, entitled "Computerized System and Method for Modifying Components of Healthcare Orders Which Are Associated Into Cross-Phase Groups", each of which was filed on even date herewith.

STATEMENT REGARDING FEDERALLY SPONSORED RESEARCH OR DEVELOPMENT

Not Applicable.

BACKGROUND

Healthcare orders are requests placed by healthcare providers for, e.g., procedures, medications, laboratory tests, evaluations, treatments, and nursing tasks to be done for a patient. In a non-electronic healthcare order system, orders from different categories in one healthcare plan (such as medications, labs, diagnostic tests, and nursing orders) are generally documented on a single piece of paper. A healthcare plan includes multiple orders for treatment for a particular problem or ailment. For example, a healthcare plan for a cancer patient may include multiple medication orders and laboratory testing orders. Once these orders are reviewed by a healthcare provider, the necessary orders for different categories are forwarded to the correct location to be completed or filled. For example, if one order includes a medication, a medication paper order may be sent to the pharmacy to be filled. If one of the orders in the healthcare plan is for a laboratory test, a paper laboratory requisition form may be sent to the laboratory. In the paper healthcare ordering system, it is typically possible to go back to the original paper order set containing all of the orders for the healthcare plan. An example of a healthcare plan or procedure would be a chemotherapy protocol that includes multiple orders for medications, laboratory tests, and diagnostic tests.

In an electronic healthcare order environment, if a set of orders is placed for a healthcare plan, once the orders have been reviewed they are electronically dispersed to the appropriate location, such as the pharmacy or laboratory application. U.S. patent application Ser. Nos. 11/022,540, 11/020, 489, and 11/021,509 (each of which is incorporated herein by reference) describe methods and systems for creating and maintaining associations among the orders in a healthcare plan in a computerized environment such that the associations may be accessed and viewed after one or more of the orders is distributed to the proper application to be filled.

Often times, an order (or set of orders) will set forth a healthcare plan having components which span multiple phases. For instance, a healthcare plan for a chemotherapy protocol may specify that a particular medication is to be given in a specified dosage on three separate days, e.g., Day 1, Day 8, and Day 15. In this instance, each day may be viewed as a separate phase. Phases, however, are not limited to units of time. In simple terms, a phase is merely a plan within a plan and, accordingly, may be a unit of time, a diagnostic grouping, or any other sub-plan within a healthcare plan.

In an electronic healthcare order environment, when an order (or set of orders) spans multiple phases, each component of each phase appears to a user as a separate order. More importantly, each component of each phase appears to the electronic environment as a separate order. This means that each component of each phase must be entered into the electronic system separately and any modification to a particular component must be entered for that component in each of the phases in which it may appear. For instance, in the above chemotherapy protocol example, if it is desired to modify the dosage of the medication that is to be given to the patient on each of Days 1, 8, and 15, such modification must be separately entered for each of the three phases. Such duplicate entering is not only inefficient but increases the possibility of human error.

Accordingly, a system and method for associating components which span multiple phases of a healthcare plan would be desirable. Additionally, a system and method for modifying a component such that any modification thereto is also applied to all components associated therewith would be advantageous. Further, it would be advantageous if such modifications could be entered one time instead of once for each phase to which they apply.

BRIEF SUMMARY

Embodiments of the present invention relate to methods in a clinical computing environment for verifying authority to modify at least one clinical order. In one embodiment, the method includes receiving the at least one clinical order, the order having components associated with a plurality of phases; associating a plurality of the components to form a cross-phase group, the plurality of components including at least a component associated with a first phase and a component associated with a second phase, wherein each of the components in the cross-phase group includes a common attribute; receiving a user indication to modify the common attribute of the component associated with the first phase; and determining whether a user from whom the user indication is received has the authority to modify the common attribute of the component associated with the first phase. If it is determined that the user has the authority to modify the common attribute of the component associated with the first phase, the method may further include modifying all components that are associated in the cross-phase group in response to the indication received. If, however, it is determined that the user does not have the authority to modify the common attribute of the component associated with the first phase, the method may further include not modifying the common attribute in response to the indication received and/or displaying a message indicating that the attribute will not be modified in response to the indication received.

Embodiments of the present invention additionally relate to one or more computer readable media having computer-executable instructions for performing the methods described, as well as to computers programmed to perform such methods.

Embodiments of the present invention further relate to systems in a clinical computing environment for verifying authority to modify a clinical order. In one embodiment, the system includes an order receiving element for receiving at least one clinical order having components associated with a plurality of phases; an associating element for associating a plurality of the components to form a cross-phase group, the components including at least a component associated with a first phase and a component associated with a second phase, wherein each of the components in the cross-phase group includes a common attribute; an indication receiving element for receiving a user indication to modify the common attribute of the component associated with the first phase; and a determining element for determining whether a user from whom the user indication is received has the authority to modify the common attribute of the component associated with the first phase. If it is determined that the user from whom the indication is received has the authority to modify the common attribute, the system may further include a modifying element for modifying all components that are associated in the cross-phase group in response to the indication received. If, however, it is determined that the user from whom the indication is received does not have the authority to modify the common attribute, the system may further include a displaying element for displaying a message indicating that the common attribute will not be modified in response to the indication received.

In another embodiment, a system in accordance with the present invention includes order receiving means for receiving the at least one clinical order, the at least one clinical order having components associated with a plurality of phases; associating means for associating a plurality of the components to form a cross-phase group, the plurality of the components including at least a component associated with a first phase and a component associated with a second phase, wherein each of the components in the cross-phase group includes a common attribute; indication receiving means for receiving a user indication to modify the common attribute of the component associated with the first phase; and determining means for determining whether a user from whom the user indication is received has the authority to modify the common attribute of the component associated with the first phase. If it is determined that the user from whom the indication is received has the authority to modify the common attribute, the method may further include modifying means for modifying all components that are associated in the cross-phase group in response to the indication received. If, however, it is determined that the user from whom the indication is received does not have the authority to modify the common attribute, the method may further include displaying means for displaying a message indicating that the common attribute will not be modified in response to the indication received.

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

BRIEF DESCRIPTION OF THE SEVERAL VIEWS OF THE DRAWINGS

The present invention is described in detail below with reference to the attached drawing figures, wherein:

FIG. 6 is a screen display of an exemplary view illustrating a manner in which selected attributes of a component of a cross-phase group may be modified, in accordance with an embodiment of the present invention;

FIG. 7 is a screen display of an exemplary view illustrating that when a selected detail of a component of a cross-phase group is modified as shown in FIG. 6, such modification may automatically be carried over to other components of the cross-phase group, in accordance with an embodiment of the present invention;

FIG. 8 is a screen display of an exemplary view illustrating the details of a particular phase within a healthcare plan, wherein those components that are part of a cross-phase group are identified by an appropriate identifier, in accordance with an embodiment of the present invention;

FIGS. 9A and 9B are screen displays of exemplary views illustrating a manner in which a component of a cross-phase group may be broken out of the group, in accordance with an embodiment of the present invention;

FIG. 10 is a screen display of an exemplary view illustrating that a component of the cross-phase group has been broken out of the group, in accordance with an embodiment of the present invention;

FIG. 11 is a screen display of an exemplary view illustrating a manner in which an attribute of a component of a cross-phase group may be modified, in accordance with an embodiment of the present invention;

FIG. 12 is a screen display of an exemplary view illustrating an alert that may be presented to a user upon attempting to modify a component which is a part of a cross-phase group, in accordance with an embodiment of the present invention;

FIG. 13 is a screen display of an exemplary view illustrating that the modification implemented in the screen display of FIG. 11 may be applied to all components of the cross-phase group except for those components which have been broken out of the group, in accordance with an embodiment of the present invention;

FIG. 14 is a screen display of an exemplary view from which a particular phase of a cross-phase group may be initiated, in accordance with an embodiment of the present invention; and FIG. 15 is a screen display of an exemplary view illustrating a particular phase of a cross-phase group that has been initiated but still needs to be signed, in accordance with an embodiment of the present invention.

DETAILED DESCRIPTION

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different components of methods employed, the terms should not be interpreted as implying any particular order among or between various steps herein disclosed unless and except when the order of individual steps is explicitly described.

Embodiments of the present invention provide computerized methods and systems for modifying at least one component of a clinical order. Embodiments of the present invention further provide computerized methods and systems for modifying at least one component of a clinical order, wherein a plurality of components derived from the clinical order are associated with one another to form a cross-phase group. Still further, embodiments of the present invention provide computerized methods and systems for modifying at least one component of a clinical order, wherein a plurality of components derived from the clinical order are associated to form a cross-phase group, and wherein at least one of the associated components has been broken out of the group. An exemplary operating environment is described below.

Figure 1:
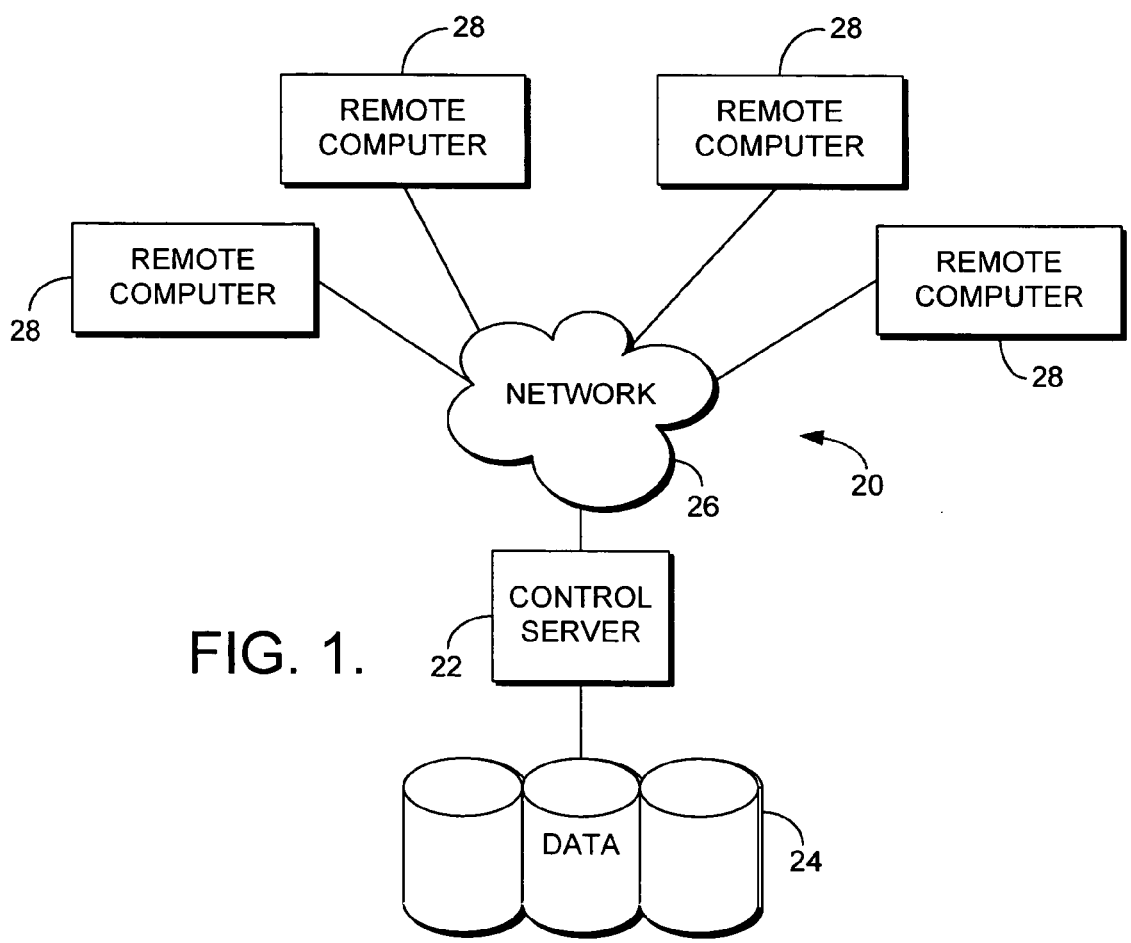
FIG. 1 is a block diagram of an exemplary computing environment suitable for use in implementing the present invention.

Referring to the drawings in general, and initially to FIG. 1 in particular, an exemplary computing system environment, for instance, a medical information computing system, on which embodiments of the present invention may be implemented is illustrated and designated generally as reference numeral 20. It will be understood and appreciated by those of ordinary skill in the art that the illustrated medical information computing system environment 20 is merely an example of one suitable computing environment and is not intended to suggest any limitation as to the scope of use or functionality of the invention. Neither should the medical information computing system environment 20 be interpreted as having any dependency or requirement relating to any single component or combination of components illustrated therein.

Embodiments of the present invention may be operational with numerous other general purpose or special purpose computing system environments or configurations. Examples of well-known computing systems, environments, and/or configurations that may be suitable for use with embodiments of the present invention include, by way of example only, personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

Embodiments of the present invention may be described in the general context of computer-executable instructions, such as program modules, being executed by a computer. Generally, program modules include, but are not limited to, routines, programs, objects, components, and data structures that perform particular tasks or implement particular abstract data types. The present invention may also be practiced in distributed computing environments where tasks are performed by remote processing devices that are linked through a communications network. In a distributed computing environment, program modules may be located in local and/or remote computer storage media including, by way of example only, memory storage devices.

With continued reference to FIG. 1, the exemplary medical information computing system environment 20 includes a general purpose computing device in the form of a server 22. Components of the server 22 may include, without limitation, a processing unit, internal system memory, and a suitable system bus for coupling various system components, including database cluster 24, with the server 22. The system bus may be any of several types of bus structures, including a memory bus or memory controller, a peripheral bus, and a local bus, using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The server 22 typically includes, or has access to, a variety of computer readable media, for instance, database cluster 24. Computer readable media can be any available media that may be accessed by server 22, and includes volatile and nonvolatile media, as well as removable and non-removable media. By way of example, and not limitation, computer readable media may include computer storage media and communication media. Computer storage media may include, without limitation, volatile and nonvolatile media, as well as removable and nonremovable media implemented in any method or technology for storage of information, such as computer readable instructions, data structures, program modules, or other data. In this regard, computer storage media may include, but is not limited to, RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the server 22. Communication media typically embodies computer readable instructions, data structures, program modules, or other data in a modulated data signal, such as a carrier wave or other transport mechanism, and may include any information delivery media. As used herein, the term "modulated data signal" refers to a signal that has one or more of its attributes set or changed in such a manner as to encode information in the signal. By way of example, and not limitation, communication media includes wired media such as a wired network or direct-wired connection, and wireless media such as acoustic, RF, infrared, and other wireless media. Combinations of any of the above also may be included within the scope of computer readable media.

The computer storage media discussed above and illustrated in FIG. 1, including database cluster 24, provide storage of computer readable instructions, data structures, program modules, and other data for the server 22.

The server 22 may operate in a computer network 26 using logical connections to one or more remote computers 28. Remote computers 28 may be located at a variety of locations in a medical or research environment, for example, but not limited to, clinical laboratories, hospitals and other inpatient settings, veterinary environments, ambulatory settings, medical billing and financial offices, hospital administration settings, home health care environments, and clinicians' offices. Clinicians may include, but are not limited to, a treating physician or physicians, specialists such as surgeons, radiologists, cardiologists, and oncologists, emergency medical technicians, physicians' assistants, nurse practitioners, nurses, nurses' aides, pharmacists, dieticians, microbiologists, laboratory experts, genetic counselors, researchers, veterinarians, students, and the like. The remote computers 28 may also be physically located in non-traditional medical care environments so that the entire health care community may be capable of integration on the network. The remote computers 28 may be personal computers, servers, routers, network PCs, peer devices, other common network nodes, or the like, and may include some or all of the components described above in relation to the server 22. The devices can be personal digital assistants or other like devices.

Exemplary computer networks 26 may include, without limitation, local area networks (LANs) and/or wide area networks (WANs). Such networking environments are commonplace in offices, enterprise-wide computer networks, intranets, and the Internet. When utilized in a WAN networking environment, the server 22 may include a modem or other means for establishing communications over the WAN, such as the Internet. In a networked environment, program modules or portions thereof may be stored in the server 22, in the database cluster 24, or on any of the remote computers 28. For example, and not by way of limitation, various application programs may reside on the memory associated with any one or more of the remote computers 28. It will be appreciated by those of ordinary skill in the art that the network connections shown are exemplary and other means of establishing a communications link between the computers (e.g., server 22 and remote computers 28) may be utilized.

In operation, a user may enter commands and information into the server 22 or convey the commands and information to the server 22 via one or more of the remote computers 28 through input devices, such as a keyboard, a pointing device (commonly referred to as a mouse), a trackball, or a touch pad. Other input devices may include, without limitation, microphones, satellite dishes, scanners, or the like. Commands and information may also be sent directly from a remote healthcare device to the server 22. In addition to a monitor, the server 22 and/or remote computers 28 may include other peripheral output devices, such as speakers and a printer.

Although many other internal components of the server 22 and the remote computers 28 are not shown, those of ordinary skill in the art will appreciate that such components and their interconnection are well known. Accordingly, additional details concerning the internal construction of the server 22 and the remote computers 28 are not further disclosed herein.

Although methods and systems of embodiments of the present invention are described as being implemented in a WINDOWS operating system, operating in conjunction with an Internet-based system, one of ordinary skill in the art will recognize that the described methods and systems can be implemented in any system supporting the receipt and processing of healthcare orders. As contemplated by the language above, the methods and systems of embodiments of the present invention may also be implemented on a stand-alone desktop, personal computer, or any other computing device used in a healthcare environment or any of a number of other locations.

Figure 2:
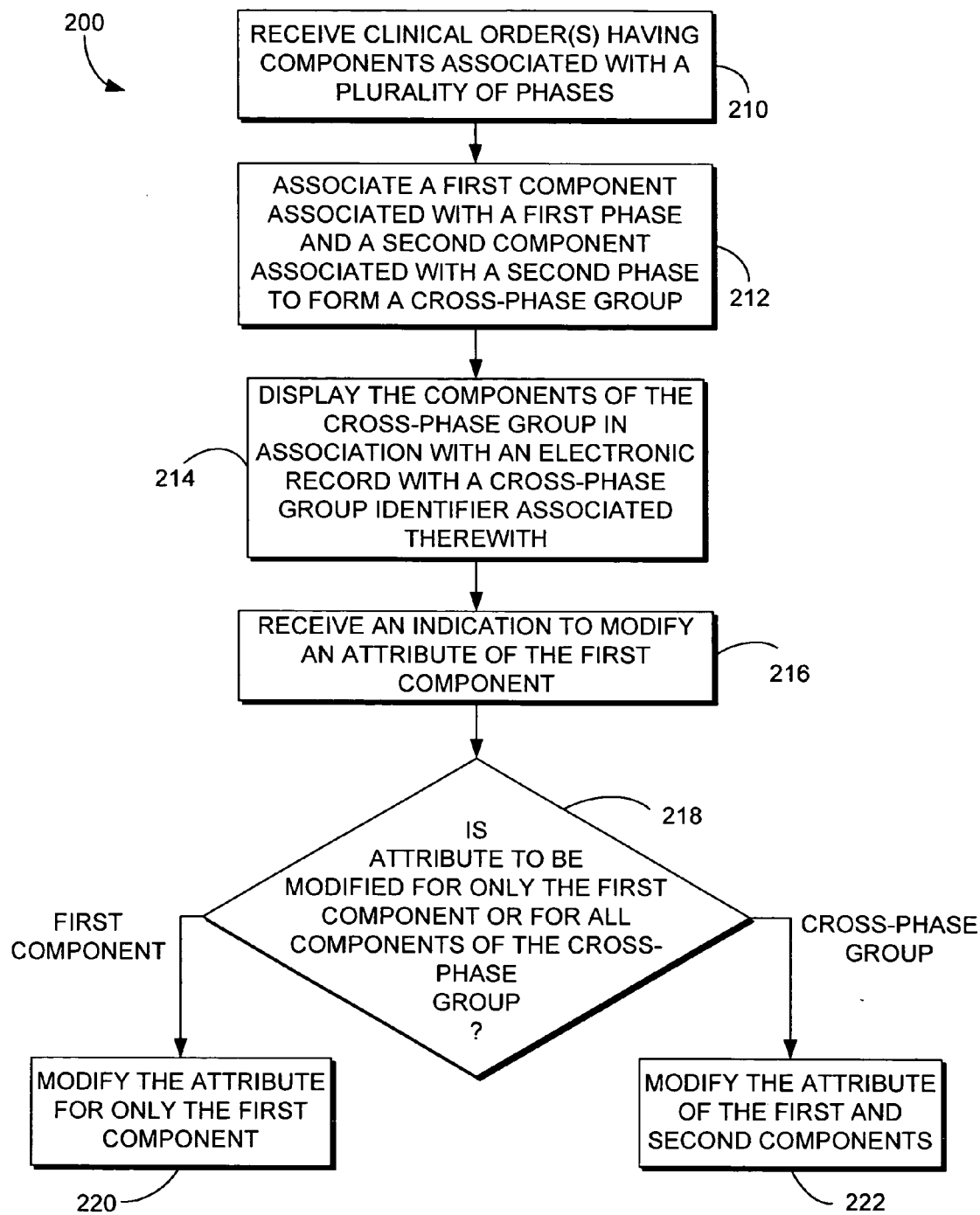
FIG. 2 is a flow diagram showing a method for modifying at least one component of a clinical order, wherein a plurality of components derived from the clinical order are associated to form a cross-phase group, in accordance with an embodiment of the present invention.

As previously mentioned, in one embodiment, the present invention relates to a computerized method and system for use in, e.g., a healthcare computing environment, for modifying at least one component of a clinical order. With reference to FIG. 2, a flow chart representative of such a method in accordance with an embodiment of the present invention is illustrated and depicted generally as reference numeral 200. Method 200 may be implemented on the above-described exemplary computing system environment (FIG. 1) and, by way of example only, may be utilized by a clinician to modify one or more components of a clinical order which spans a plurality of phases within a healthcare plan for a particular patient. (The terms "individual", "person", and "patient" are used interchangeably herein and are not meant to limit the nature of the referenced individual in any way. Rather, the methods and systems described herein are equally applicable in, for instance, a veterinary setting. Further, use herein of the term "patient" is not meant to imply any particular relationship between the individual and those modifying component(s) of a clinical order.)

Initially, as shown at block 210, the system receives one or more clinical orders having components that are associated with a plurality of phases. For instance, a healthcare plan containing a chemotherapy protocol for a patient may specify that a particular medication, cyclophosphamide, is to be administered to the patient in a normalized dose of 500 mg/m$^2$ on each of Day 1, Day 8, and Day 15 of treatment. In this instance, each of Day 1, Day 8, and Day 15 are different phases and the particular medication, cyclophosphamide, is the component associated with each phase. Administration instructions for each phase may be included in three separate orders or may be included in a single order.

Next, as shown at block 212, at least a first component associated with a first phase and a second component associated with a second phase are associated with one another to form a cross-phase group. Returning to the above-described example, cyclophosphamide is the first component associated with the first phase (Day 1) and cyclosphosphamide is the second component associated with the second phase (Day 8). It will be understood and appreciated by those of ordinary skill in the art that the first and second components will often be the same component but this will not necessarily always be the case. It is contemplated within the scope of embodiments of the present invention that components associated with different phases may be the same component or different components. Alternatively, the first phase and the second phase will in all instances be separate phases.

Figure 5A:
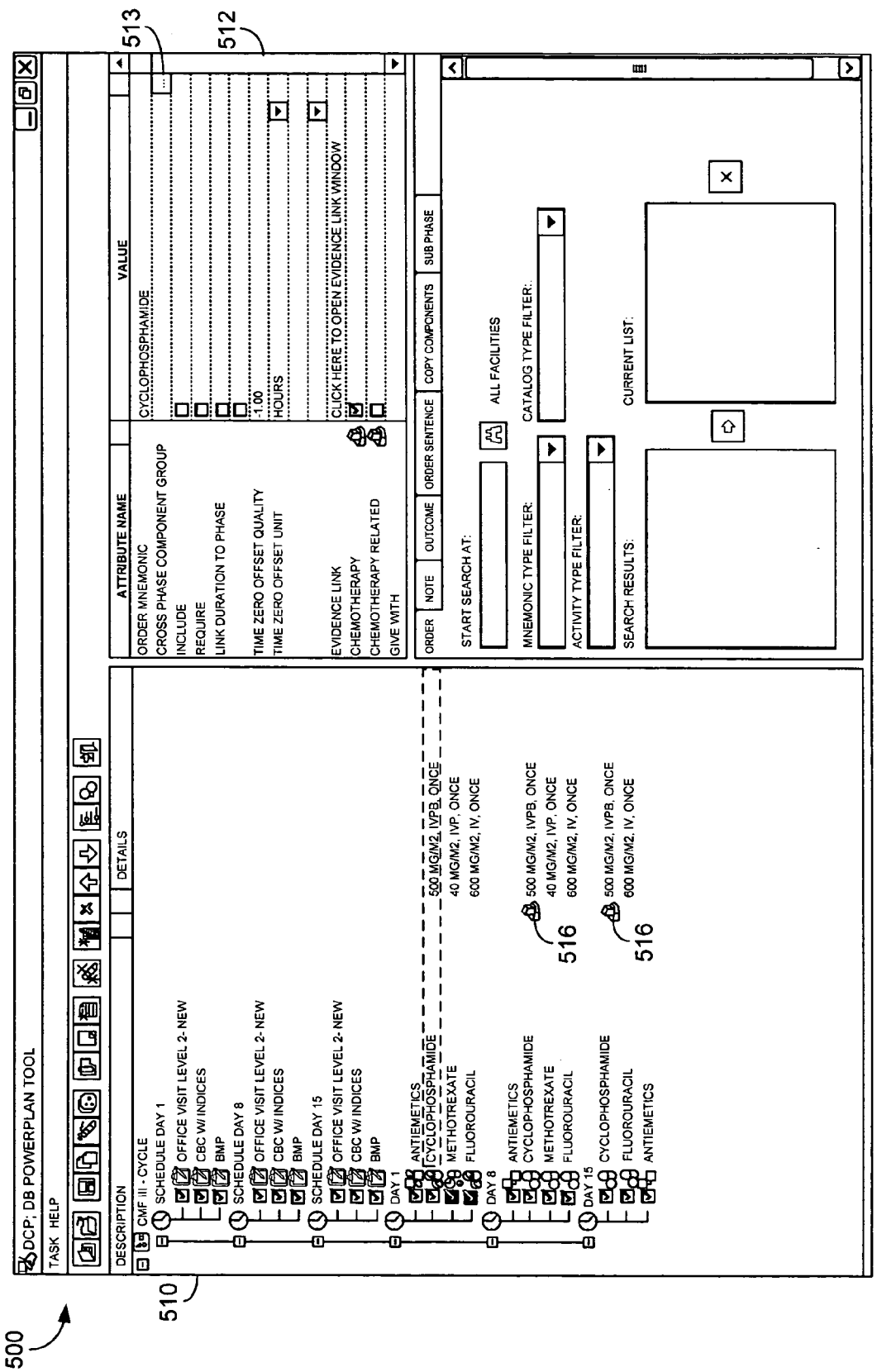
FIGS. 5A-5C are screen displays of exemplary views illustrating a manner in which components may be associated with one another to form a cross-phase group, in accordance with an embodiment of the present invention.
Figure 5B:
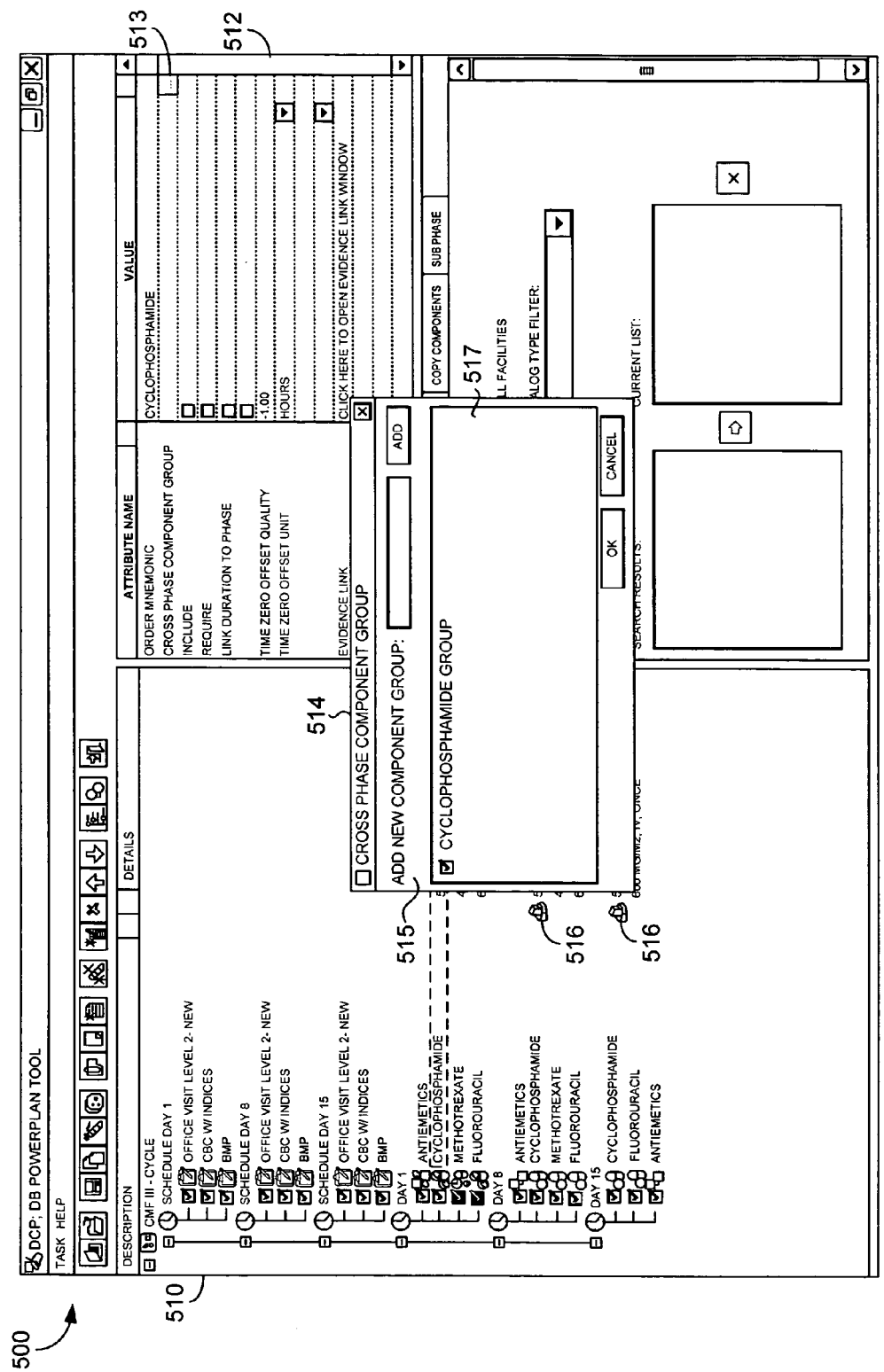
Figure 5C:
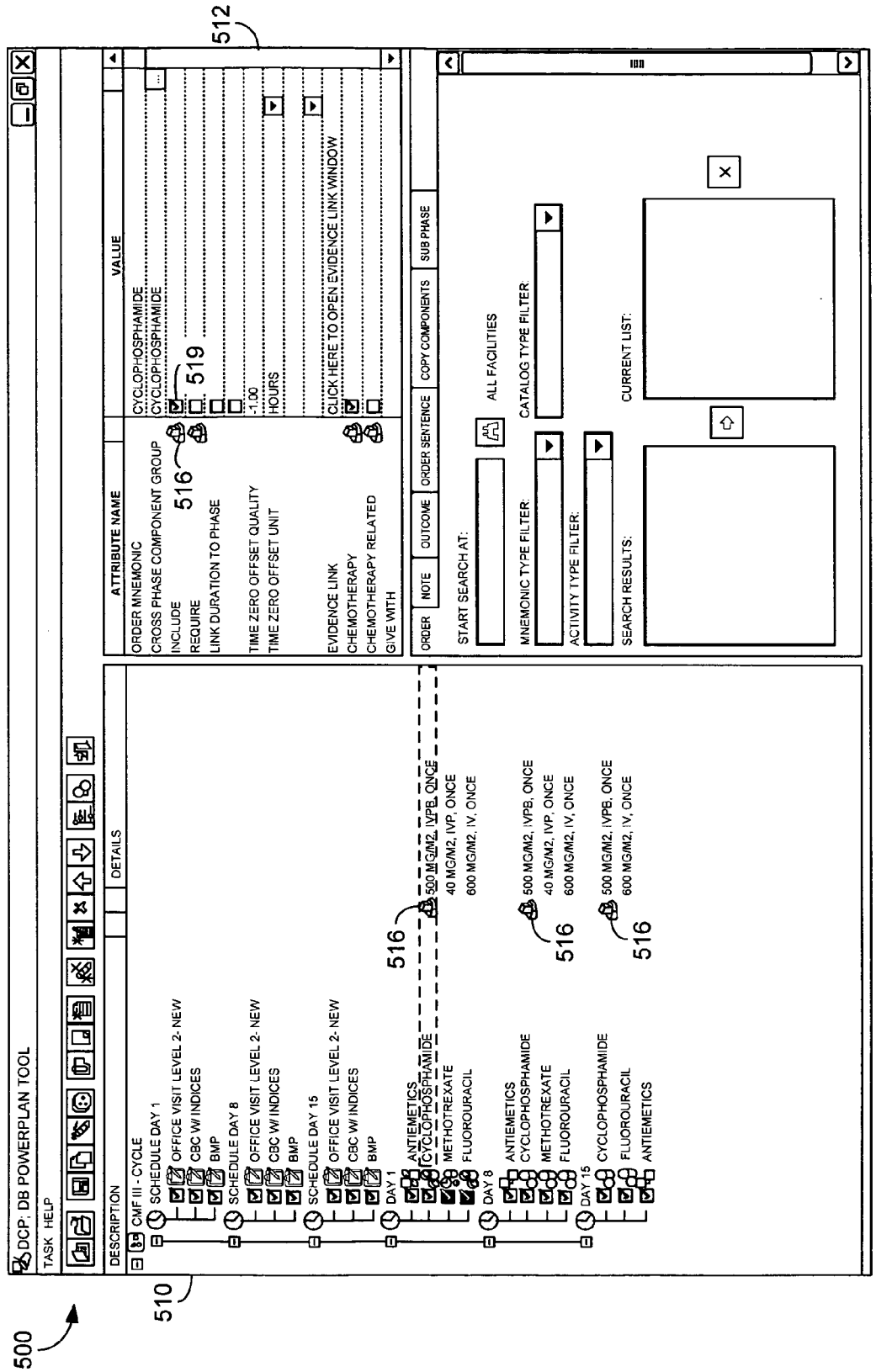

Referring to FIGS. 5A-5C, screen displays of exemplary views illustrating a manner in which components associated with different phases may be associated with one another to form a cross-phase group in accordance with an embodiment of the present invention is shown and designated generally as reference numeral 500. Screen display 500 includes a navigation portion 510 and a cross-phase group details portion 512. All orders associated with the "CMF III-CYCLE" plan that have already been received by the system are illustrated in the navigation portion 510 in association with the phase or phases to which they apply. The navigation portion 510 permits a user to select a particular component from a particular phase and view and/or alter details concerning that component/phase combination in the cross-phase group details portion 512. In the illustrated embodiment, a user has selected the medication component cyclophosphamide associated with Day 1 (first phase). Accordingly, the details of such component/phase combination are shown in the cross-phase group details portion 512.

With reference to FIG. 5A, to associate a component with one or more components in an existing cross-phase group, or to create an association for a new cross-phase group, the user may select expansion selector 513. Such selection may cause, e.g., dialog box 514 to be displayed, as shown in FIG. 5B. Dialog box 514 includes a new component addition area 515 and an existing cross-phase group display area 517. To create an association for a new cross-phase group, a user may insert the desired title of the cross-phase group in the new component addition area 515 and select the "add" indicator. To add the component in question to an existing cross-phase group, the user may select the box associated with one of the existing cross-phase groups displayed in the existing cross-phase group display area 517 such that a check mark appears therein. In the illustrated example, the box associated with the group "cyclosphosphamide group" has been checked indicating that the user desires to add the component in question to the existing cyclophosphamide group.

Upon selection of the "ok" indicator, the screen display shown in FIG. 5C will be displayed. The group name "cyclophosphamide" now appears next to the "cross phase component group" indicator in the cross-phase group details portion 512. Additionally, a cross-phase group identifier 516 is now shown in association with the "include" and "require" indicators in the cross-phase group details portion 512 and in the navigation portion 510 in association with the cyclophosphamide component of the phase "Day 1". Note that the cross-phase group identifier 516 is also displayed in association with the cyclophosphamide component of each of phases "Day 8" and "Day 15" indicating each of these components is also a member of a cross-phase group. Note also, however, that without viewing the details of each of the component/phase combinations (for instance, by selection of such combinations in the navigation portion 510 of the screen display 500), a user could not be certain if all were part of the same cross-phase group. For the present example and discussion, contemplate that each of the cyclosphosphamide/Day 1, cyclosphosphamide/Day 8, and cyclosphosphamide/Day 15 component/phase combinations are included in a cross-phase group entitled "cyclosphosphamide."

It will be understood and appreciated by those of ordinary skill in the art that the default of the selection box 519 in the cross-phase group details portion 512 may be for inclusion or exclusion of the component/phase combination selected from the navigation portion 510, as desired. An "included" component is associated with the group and will be ordered and given in accordance with the cross-phase group details. An "excluded" component is also associated with the cross-phase group but will not be ordered or given. Modification to any component of the cross-phase group will be applied to both included or excluded components as long as such component has not been broken out of the group or dithered. Modification, breaking out, and dithering of components are described more fully below.

Referring back to FIG. 2, those components selected for association in the cross-phase group are subsequently displayed in association with an electronic record, e.g., an electronic medical record generated by Cerner Millennium available from Cerner Corporation of North Kansas City Mo. Additionally displayed is the cross-phase group identifier in association with the components included in the cross-phase group. This is indicated at block 214.

With reference to FIG. 5, note that a number of attributes other than inclusion/exclusion may be defined in cross-phase group details portion 512. For those attributes shown in association with a cross-phase group identifier 516 (e.g., chemotherapy, chemotherapy related, etc.), any modification made thereto will likewise be made for all other component/phase combinations in the cross-phase group unless such components have been broken out or dithered, as more fully described below. Alternatively, for those attributes shown without an associated cross-phase group identifier (e.g., time zero offset quality, etc.), any modification made thereto will be applied only to the component for which details are shown in the cross-phase group details portion 512. In this way, the illustrated association tool permits single entry of those attributes that are set up to apply to all members of a cross-phase group yet still permits individual entry/modification of those attributes for which independent setting may be desired.

Referring back to FIG. 2, an indication to modify an attribute of the first component is subsequently received, as indicated at block 216. In those instances where the first component is a medication, attributes thereof may include those details that a clinician may include in a medication order. By way of example only, and not limitation, such details may include a medication identifier, medication dosage, medication form, frequency of administration, and route of administration.

Figure 6:
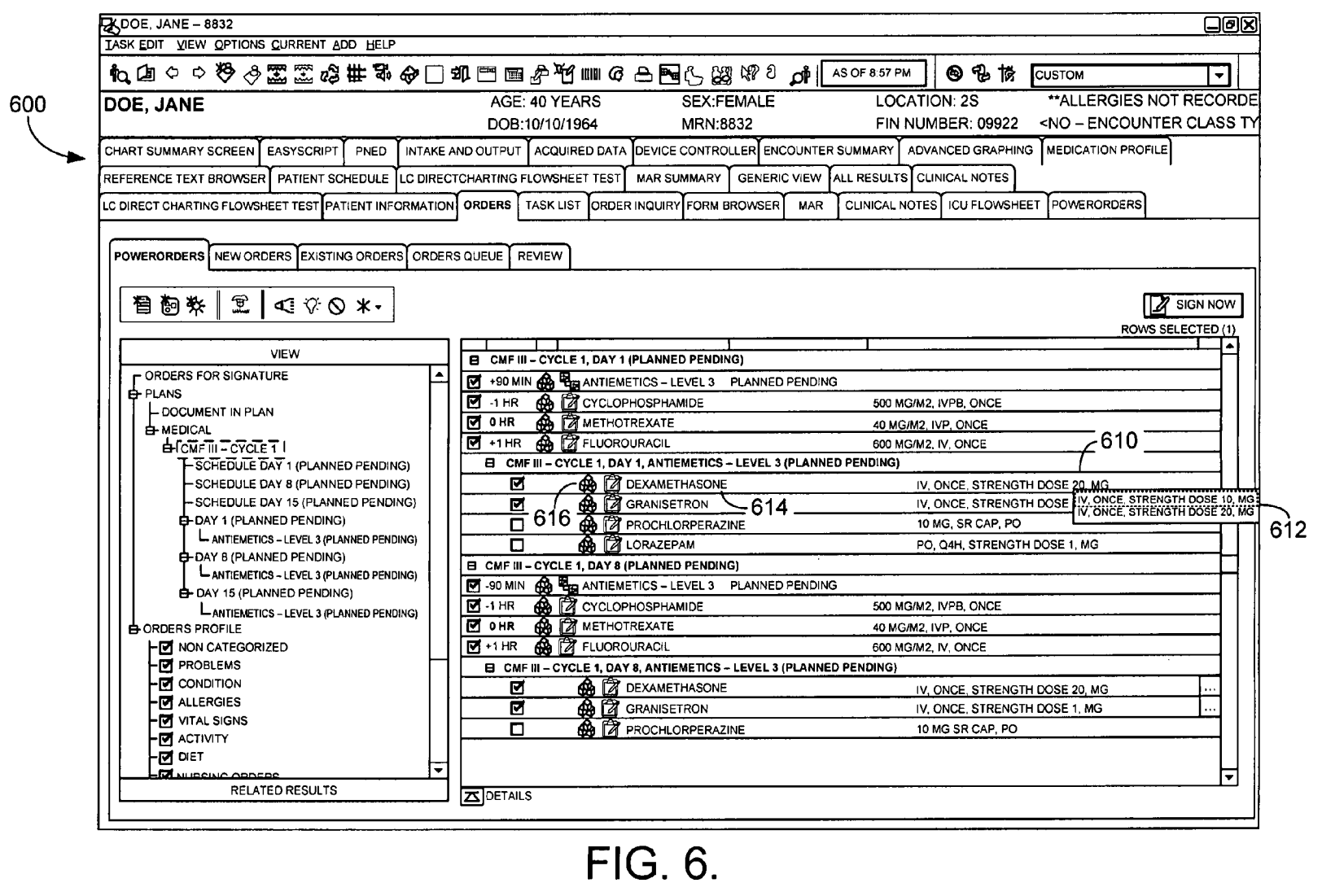

With reference to FIG. 6, a screen display of an exemplary view illustrating a manner in which selected attributes of a component which is a member of a cross-phase group may be modified in accordance with an embodiment of the present invention is shown and designated generally as reference numeral 600. In the illustrated example, the attribute being modified is the dosage of the component medication dexamethasone to be administered on Day 1. Prior to an indication of a desired modification being received, the dosage of dexamethasone to be administered during the first phase (Day 1) is 20 mg, as shown in the text box 610.

In the illustrated screen display 600, the indication to modify the dosage of dexamethasone to be administered on Day 1 is received by user selection of a different dosage from a pre-determined list of dosages shown in a drop-down menu 612. This is an example of a modification being made at the order sentence level from a recommended list of clinically appropriate alternatives. Modifications may also be made at the details level, as more fully described below with reference to FIG. 11. Drop-down menu 612 may be accessed, for instance, by a user placing a pointer over the text box 610 and pressing the right-hand button of a mouse. Once the drop-down menu 612 is accessed, the user may select a different pre-determined dosage, in this case 10 mg, to indicate that a modification in the administered dosage is requested. In screen display 600, a dosage of 10 mg is selected by a user from the drop-down menu 612 selections and such indication is received by the system. It will be understood and appreciate by those of ordinary skill in the art that a number of different methods for indicating a desired modification to a component may be utilized within the scope of embodiments of the present invention with a drop-down box selection being merely an example thereof. An additional example is discussed herein below with reference to FIG. 11.

Note that screen display 600 also illustrates that the dexamethasone/Day 1 component/phase combination is part of a cross-phase group, as indicated by cross-phase group identifier 616 displayed adjacent to the medication identifier 614. Further note that, although not readily apparent from screen display 600, for purposes of this example, dexamethasone/Day 8 is also included in the same cross-phase group.

Referring back to FIG. 2, it is next determined whether the indicated attribute is to be modified only for the first component or for all components included in the cross-phase group that share the attribute. This is indicated at block 218. If it is determined that the indicated attribute is to be modified only for the first component, such modification is made, as indicated at block 220. If, however, it is determined that the indicated attribute is to be modified for all components of the cross-phase group that share the attribute, the modification is made to both the first and second components, as indicated at block 222. Absent any indications to the contrary (such as a component of the cross-phase group being broken out of the group or dithered, as more fully described below), any modification made to an attribute of one component of a cross-phase group will be automatically made to all components included in the cross-phase group having the same attribute.

Figure 7:
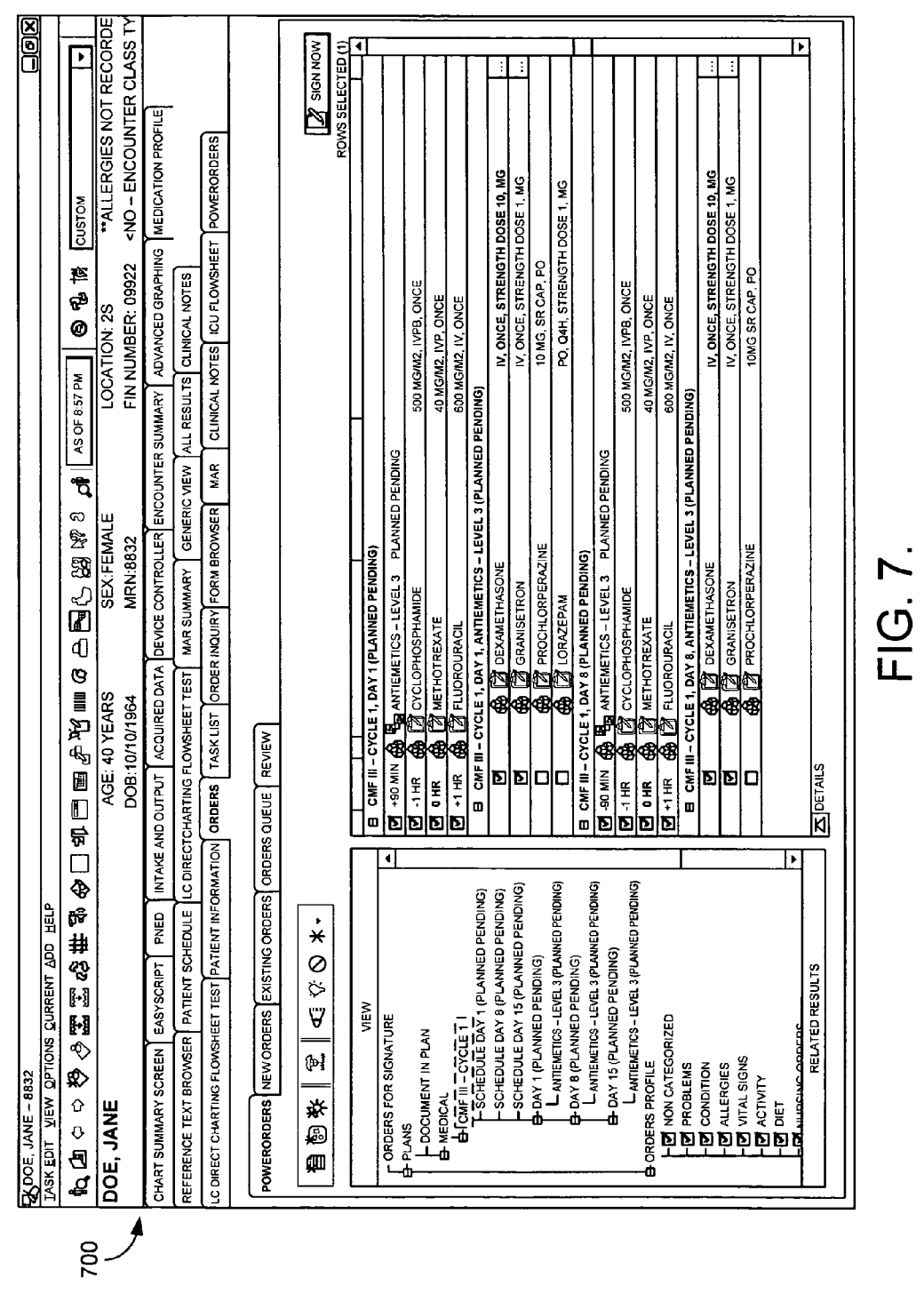

Turning now to FIG. 7, a screen display of an exemplary view illustrating that when an attribute of a component of a cross-phase group is modified as shown in screen display 600 (FIG. 6), such modification is automatically made to all components included in the cross-phase group (absent any indication to the contrary) is shown and depicted generally as reference numeral 700. It can be seen in screen display 700 that not only was the dosage modification from 20 mg to 10 mg applied to the component/phase combination dexamethasone/Day 1 but also to the component/phase combination dexamethasone/Day 8, as dexamethasone to be administered on Day 8 is a component of the same cross-phase group as dexamethasone to be administered Day 1. Note that the requested modification was received only once (and, accordingly, entered only once by a user) and yet may be applied to all components associated in the cross-phase group by virtue of the association set forth at block 212.

It should be noted that while the above-described association of components, as well as modification of attributes thereof, has been described on a per-component basis, the methods are equally applicable with respect to embedded sub-phases. For instance, with reference to FIG. 6, it can be seen that under the heading "CMF III-Cycle 1, Day 1 (Planned Pending)", there is a component sub-phase entitled "Antiemetics-Level 3". It is apparent to a user that this is an component sub-phase rather than a single component as more detailed information regarding the Level 3 antiemetics is displayed separately under the heading "CMF III-Cycle 1, Day 1, Antiemetics-Level 3". It can also be seen that there is a cross-phase group identifier 616 displayed in association with the sub-phase identification. Any and all actions that may be taken with respect to single components which are members of a cross-phase group may also be taken with respect to embedded sub-phases which are members of a cross-phase group. Such actions include, but are not limited to, inclusion/exclusion in a cross-phase group, breaking out of a cross-phase group (as more fully described below), and modification of attributes. All such variations are contemplated to be within the scope of embodiments of the present invention.

In another embodiment, the present invention relates to a computerized method and system for use in, e.g., a healthcare computing environment, for modifying at least one component of a clinical order, wherein a plurality of components derived from the clinical order are associated to form a cross-phase group, and wherein at least one of the associated components has been broken out of the cross-phase group. A flow diagram illustrating such a method in accordance with an embodiment of the present invention is illustrated and depicted generally as reference numeral 300. Similar to method 200 of FIG. 2, method 300 may be implemented on the above-described exemplary computing system environment (FIG. 1) and, by way of example only, may be utilized by a clinician to modify at least one, but not all, of the components of a clinical order, the components spanning a plurality of phases within a healthcare plan for a particular patient.

Initially, as shown at block 310, the system receives one or more clinical orders having components associated with a plurality of phases. With reference back to the example described above with reference to FIG. 2, contemplate that a healthcare plan containing a chemotherapy protocol for a patient specifies that the medication cyclophosphamide is to be administered to the patient in a normalized dose of 500 mg/m$^2$ on each of Day 1, Day 8, and Day 15 of treatment. In this instance, each of Day 1, Day 8, and Day 15 are different phases and cyclosphophamide is the component associated with each phase. Administration instructions for each phase may be included in three separate orders or may be included in a single order.

Next, as shown at block 312, a plurality of the components are associated with one another to form a cross-phase group. For instance, a first component associated with a first phase, a second component associated with a second phase, and a third component associated with a third phase may be associated with one another to form a cross-phase group. Returning to the above-described example, cyclophosphamide is the component associated with each of the three phases, the three phases being Day 1, Day 8, and Day 15 of treatment. Again, it will be understood and appreciated by those of ordinary skill in the art that each of the plurality of components will often be the same component but this will not necessarily always be the case. It is contemplated within the scope of embodiments of the present invention that components associated with different phases may be the same component or different components. Alternatively, each of the phases associated with the plurality of components will in all instances be separate phases. Association of the components with one another may be accomplished in a number of ways including, by way of example only, as the method illustrated in screen display 500 of FIGS. 5A-5C and discussed herein above.

Figure 8:
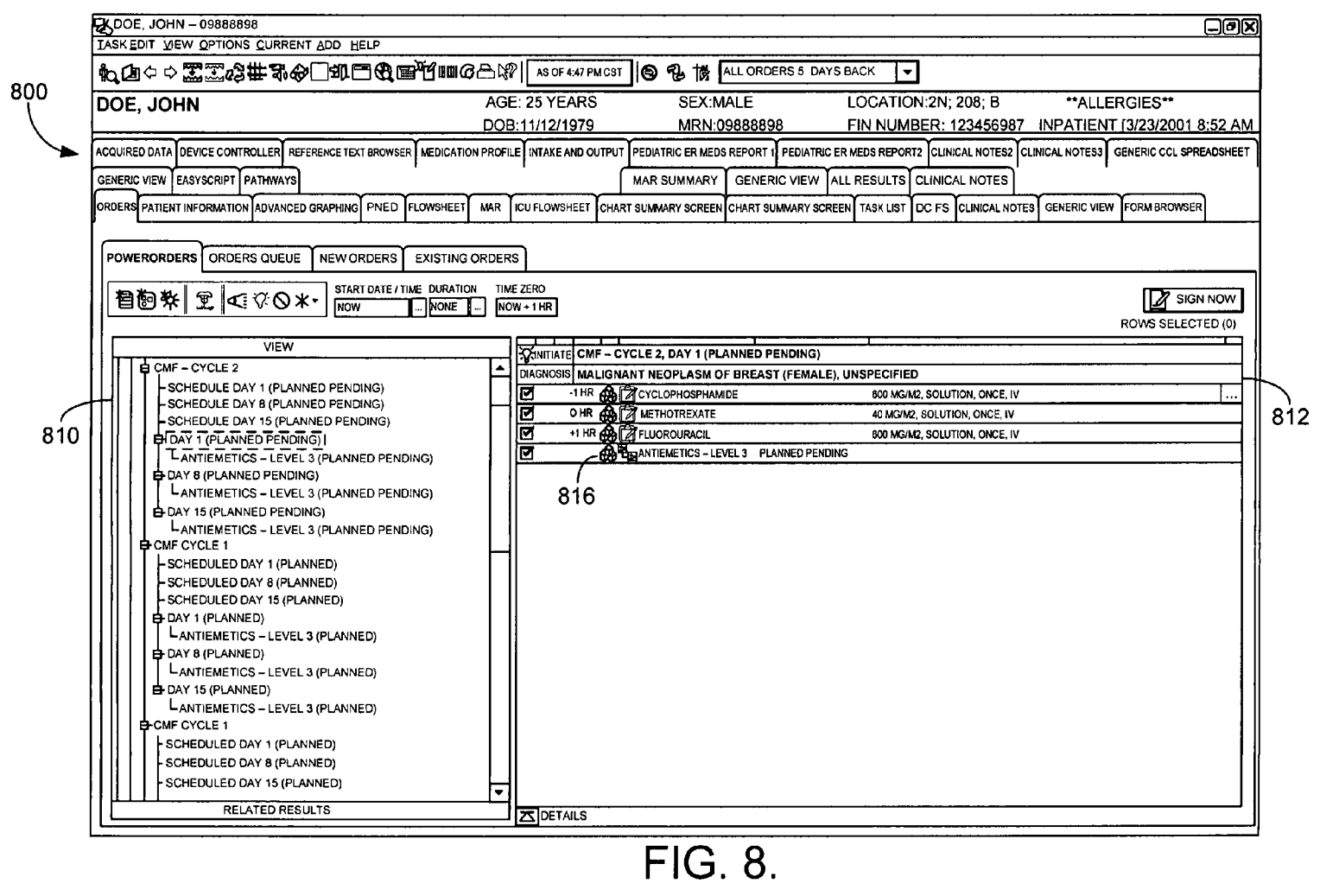

With reference to FIG. 8, a screen display 800 is shown of an exemplary view illustrating the details of a particular phase within a healthcare plan, wherein those components that are associated as part of a cross-phase group are identified by an appropriate identifier 816, in accordance with an embodiment of the present invention. Screen display 800 includes a navigation portion 810 and a phase details portion 812. All orders associated with "CMF-CYCLE 2" of the patient's healthcare plan that have already been received by the system are illustrated in the navigation portion 810 in association with the phase or phases to which they apply. The navigation portion 810 permits a user to select a particular phase (or cycle including multiple phases) and view the details of the portion of the healthcare plan that is associated with the selected phase. In the illustrated embodiment, a user has selected the phase "Day 1." Accordingly, the details of the healthcare plan that are associated with Day 1 are shown in the phase details portion 812.

Figure 9A:
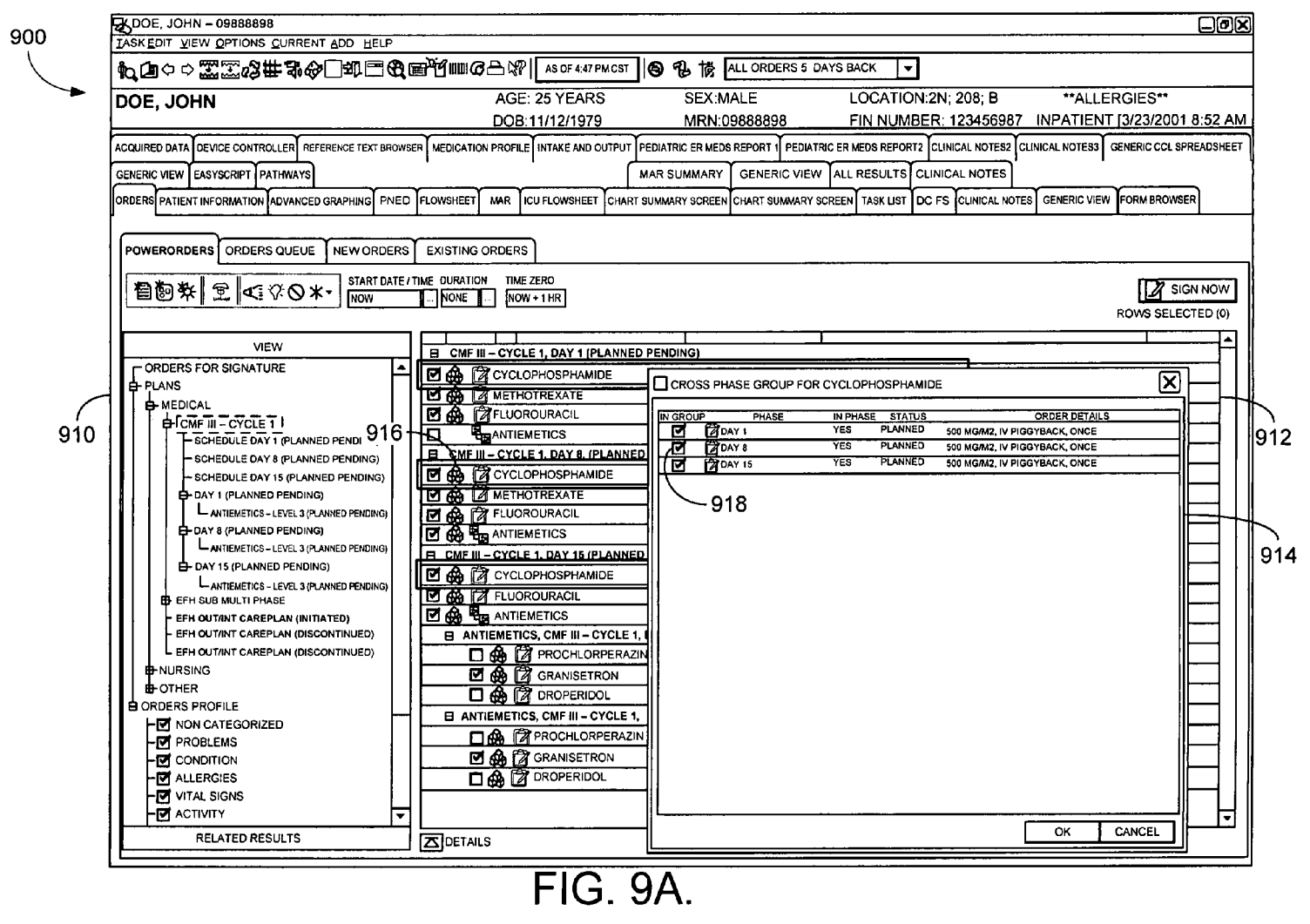

Displayed in conjunction with each component of the selected phase that is a member of a cross-phase group is a cross-phase group identifier 816. In the illustrated embodiment, each of cyclophosphamide, methotrexate, fluorouracil, and antiemetics-level 3 is identified as being associated with a cross-phase group. However, it should be noted that each of these components is associated with a different cross-phase group than the other components. As previously stated, each member of a cross-phase group is associated with a different phase. Stated differently, no two members of the same cross-phase group will be associated with the same phase. To view all members of a particular cross-phase group, a user may select the cross-phase group identifier 816 associated with the component for which s/he desires to view the group. For instance, if a user desired to view all members of the cross-phase group with which the component/phase combination cyclophosphamide/Day 1 is associated, s/he may select the cross-phase group identifier 816 associated with cyclophosphamide from the phase details portion 812 of screen display 800. An exemplary view resulting from a similar such selection is shown in the screen display 900 of FIG. 9A.

Screen display 900 includes a navigation portion 910, a phase details portion 912, and a cross-phase group details portion 914. Note that in the screen display 900 of FIG. 9A, the phase details portion 912 includes information pertaining to a number of different phases rather than a single phase as was illustrated in the screen display 800 of FIG. 8. This is because "CMF III-CYCLE 1" rather than a single phase is selected in the navigation portion 910 of FIG. 9A. Accordingly, each of the phases associated with "CMF III-CYCLE 1" are illustrated in the phase details portion 912. Note also that the phase details portion 912 includes a cross-phase group identifier 916 associated with each of the components which are associated with a cross-phase group. Selection of any of the cross-phase group identifiers 916 illustrated in association with a cyclophosphamide phase component will result in the illustrated information being shown in cross-phase group details portion 914.

Figure 9B:
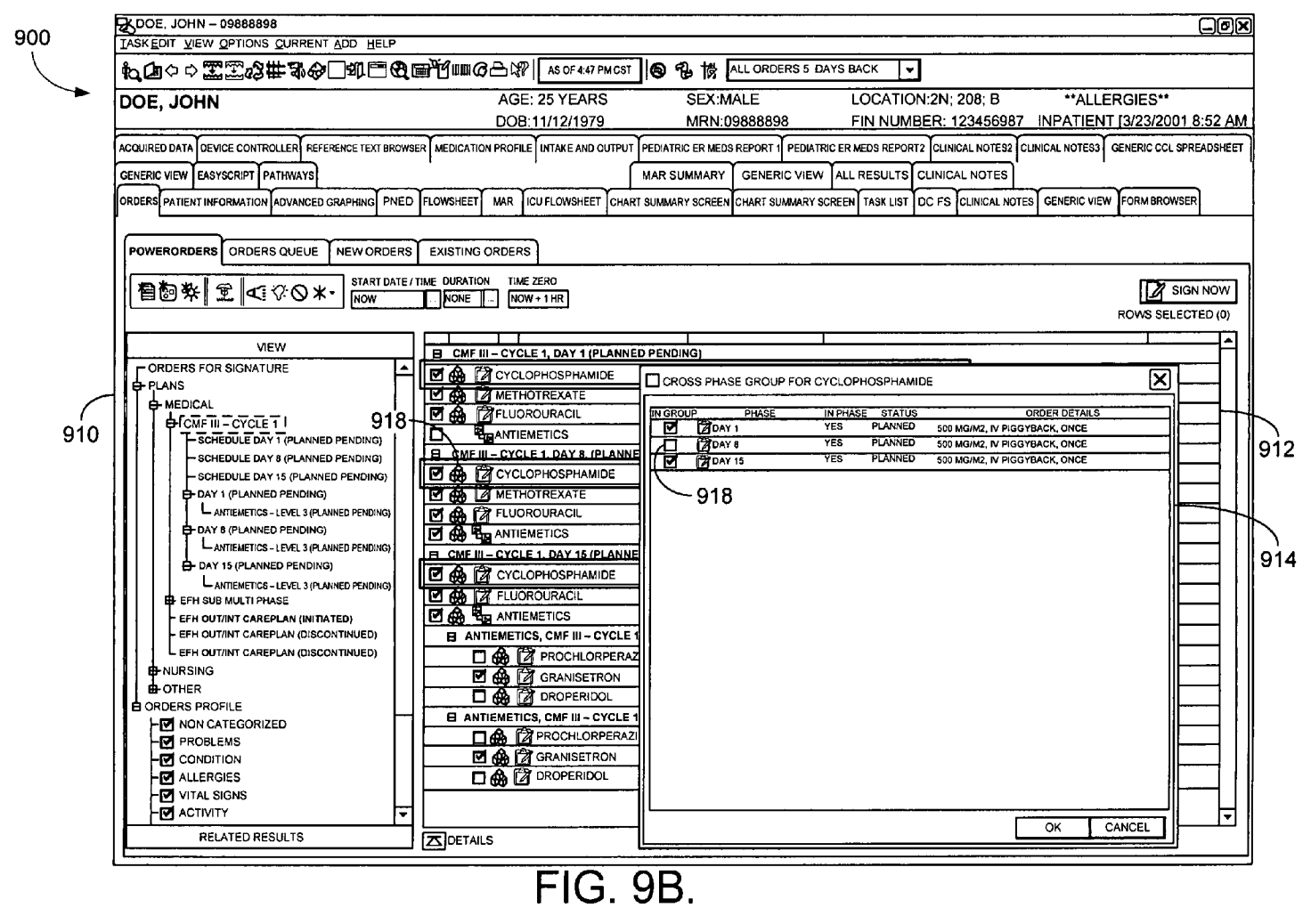

With reference back to FIG. 3, the system subsequently receives an indication to break at least one of the associated components out of the cross-phase group, as indicated at block 314. Such indication may be received, for instance, if a clinician wishes to implement a modification to some but not all of the components associated to form the cross-phase group, as more fully described below. In one embodiment, such indication may be received upon user selection of a selection box 918 associated with each member of the cross-phase group illustrated in the cross-phase group details portion 914 of FIG. 9A. For instance, contemplate that a clinician desires to break the component/phase combination cyclosphosphamide/Day 8 out of the cyclophosphamide cross-phase group. He or she may select the selection box 916 associated with Day 8 in the cross-phase group details portion 918 of FIG. 9A. Such selection would, in the illustrated instance, de-select Day 8, as shown in FIG. 9B.

With reference back to FIG. 3, in response to receiving the indication, the system breaks the at least one associated component out of the cross-phase group, as indicated at block 316. In the illustrated embodiment, the system breaks out the administration on Day 8 from the cyclosphosphamide cross-phase group.

Figure 10:
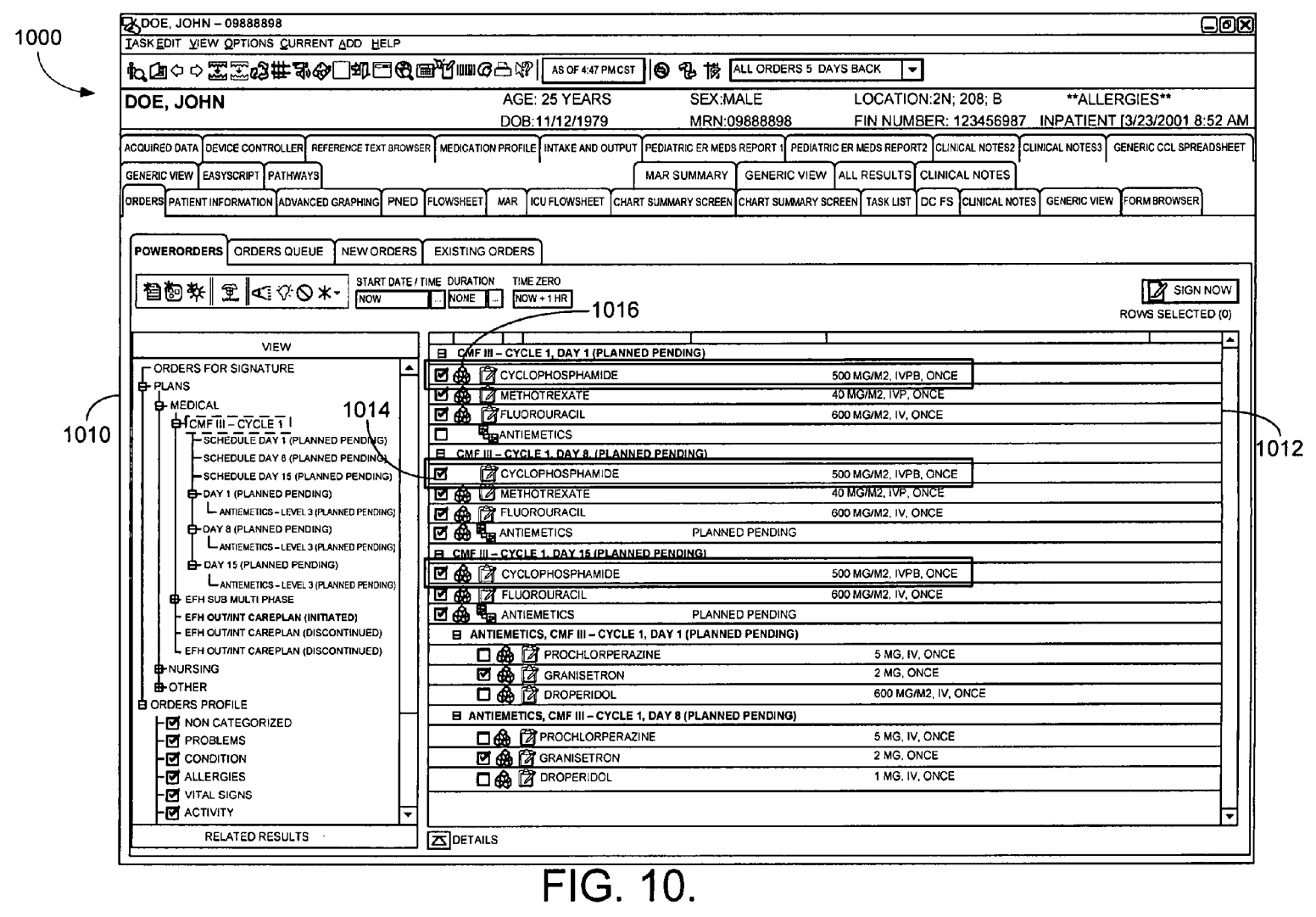

Turning now to FIG. 10, a screen display of an exemplary view illustrating that the order for cyclosphophamide on Day 8 has been broken out of the cross-phase group, in accordance with an embodiment of the present invention, is shown and designated generally as screen display 1000. Screen display 1000 includes a navigation portion 1010 and a phase details portion 1012. Displayed in association with each component which is a member of a cross-phase group is a cross-phase group identifier 1016 and an indicator box 1014. A check mark appearing in the indicator box 1014 associated with a particular component indicates that such component is included in the cross-phase group of which it is a member. As such, such component will be ordered and given in accordance with the cross-phase group details. The absence of a check mark in the indicator box 1014 associated with a particular component, however, indicates that such component has been excluded from the cross-phase group of which it is a member and thus will be neither ordered nor given. It will, however, remain associated with the cross-phase group of which it is a member. As can be seen in screen display 1000, the indicator box 1014 associated with the component/phase combination cyclophosphamide/Day 8 contains a check mark but no cross-phase group identifier in association therewith. As such, it can be seen that the component in question has been broken out of the group but will be ordered and given in accordance with the cross-phase group details as they stood at the time the component was broken out. Note that the manner in which such component/phase combination was broken out of the cross-phase group was illustrated in FIGS. 9A and 9B and discussed herein above.

Returning now to the method illustrated in the flow diagram 300 of FIG. 3, the system may subsequently receive an indication to modify an attribute of one of the components of the cross-phase group, as indicated at block 318. One exemplary manner in which such indication may be received was discussed herein above with reference to FIG. 6. Another exemplary manner in which such indication may be received is more fully described below with reference to FIG. 11. Upon receiving such indication, it is determined whether or not the component for which modification is requested is a component that has been broken out of the cross-phase group. This is indicated at block 320. If it is determined that the component for which modification is requested has not been broken out of the cross-phase group, the system modifies the attribute for all of the components in the cross-phase group except for any components which have been broken-out. This is indicated at block 322. If, however, it is determined that the component for which modification is requested has been broken out of the cross-phase group, the system modifies the attribute for only the broken-out component and not the other components in the cross-phase group.

Note that if any component associated with the component for which modification is requested has been dithered, that is, if the order containing the component has been signed (as more fully described below) or the component has otherwise been designated as past tense, the system will not modify the attribute for the dithered component. In one embodiment, the cross-phase group identifier associated with a dithered component may be displayed with an altered appearance, e.g., colored or shaded, such that status thereof may be visually determined. Selection of the cross-phase group identifier associated with a dithered component may still permit historic review of the component details, if desired.

Figure 11:
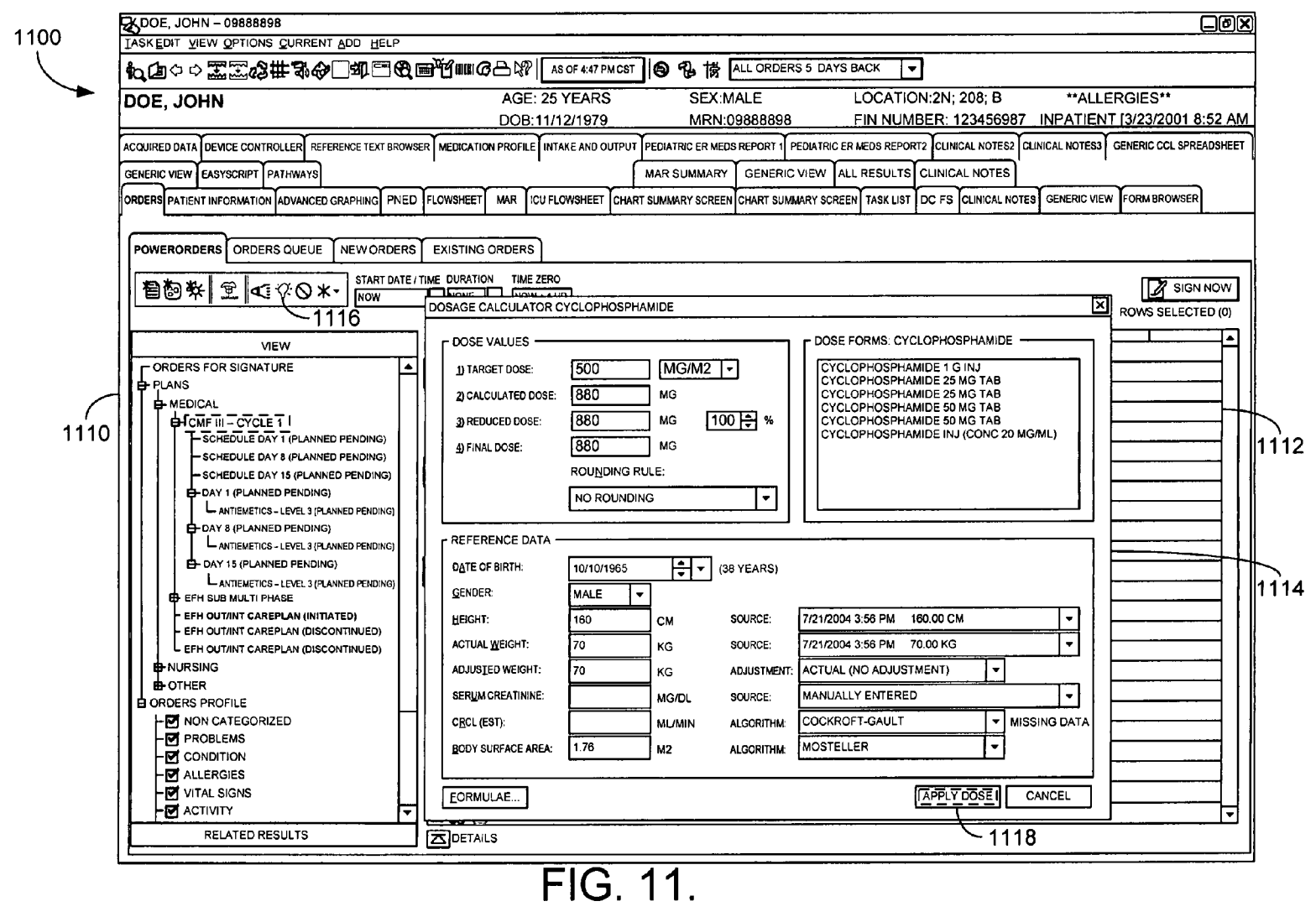

With reference to FIG. 11, a screen display of an exemplary view illustrating a manner in which an attribute of a component of a cross-phase group may be modified, in accordance with an embodiment of the present invention, is shown and depicted generally as screen display 1100. More particularly, screen display 1100 illustrates a manner in which a normalized dosage may be modified to an actual dosage for one or more components which are members of a cross-phase group. This is an example of a modification being made at the details level (as opposed to an order sentence level modification as discussed herein above with reference to FIG. 6). Screen display 1100 includes a navigation portion 1110, a phase details portion 1112, and an attribute modification portion 1114 for modifying the details of the dosage attribute. In one embodiment, attribute modification portion 1114 may be accessed by user selection of an initiation icon 1116 illustrated just above the navigation portion 1110. In another embodiment (not shown), attribute modification portion 1114 may be accessed by a user clicking the right-hand button of a conventional mouse while hovering over the normalized dosage information (not shown) of the phase details portion 1112 to display a drop-down menu which includes a menu option "modify prior to initiate," or the like.

Once accessed, relevant reference data concerning the patient for whom the actual dosage is being calculated may be entered into the appropriate fields of the attribute modification portion 1114. Upon completing entry of the relevant reference data, a user may select the "apply dose" indicator 1118 to apply the actual dosage to the component or components for which the dosage attribute was modified.

Figure 3:
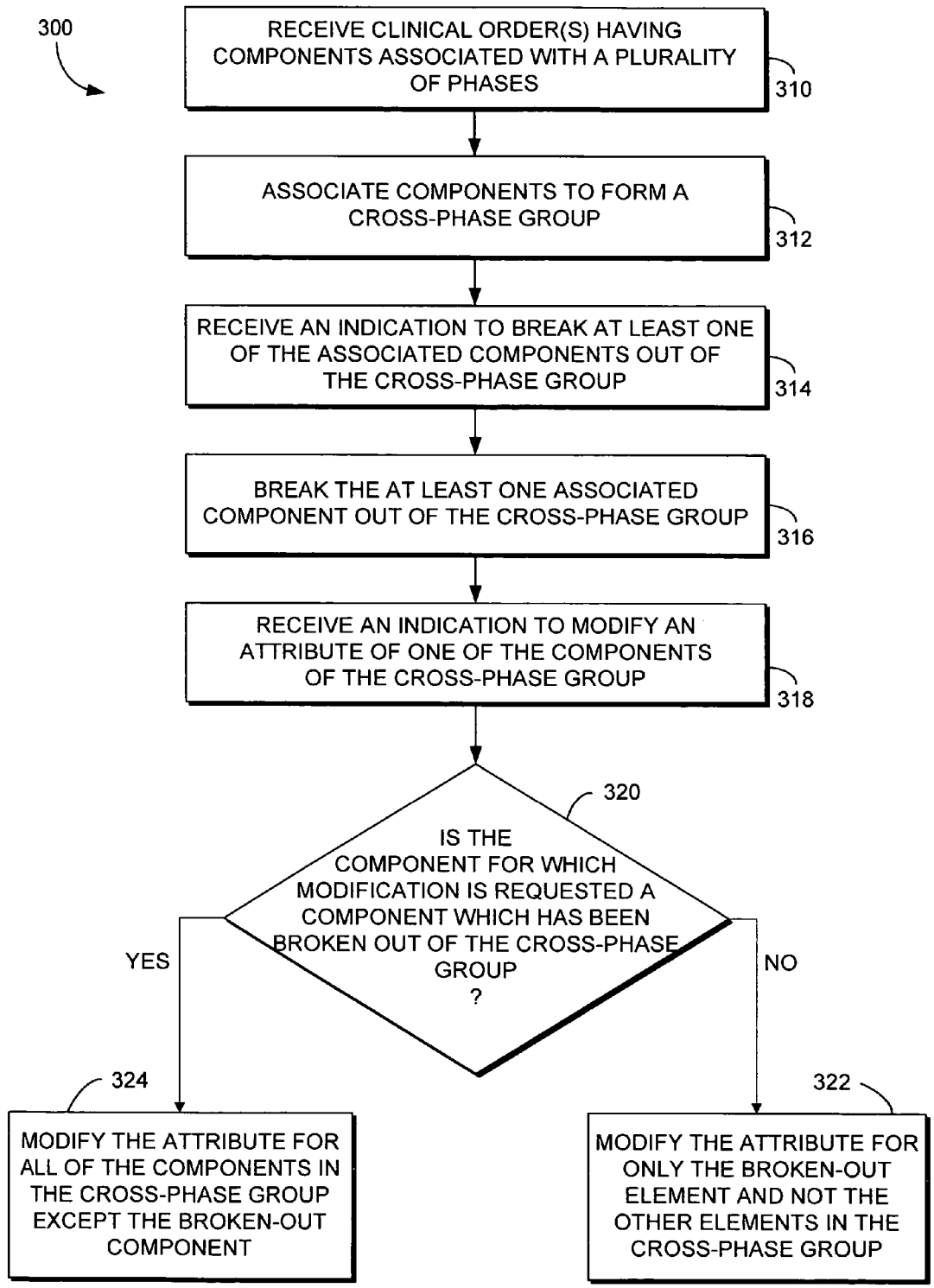
FIG. 3 is a flow diagram showing a method for modifying at least one component of a clinical order, wherein a plurality of components derived from the clinical order are associated to form a cross-phase group, and wherein at least one of the associated components has been broken out of the cross-phase group, in accordance with an embodiment of the present invention.
Figure 12:
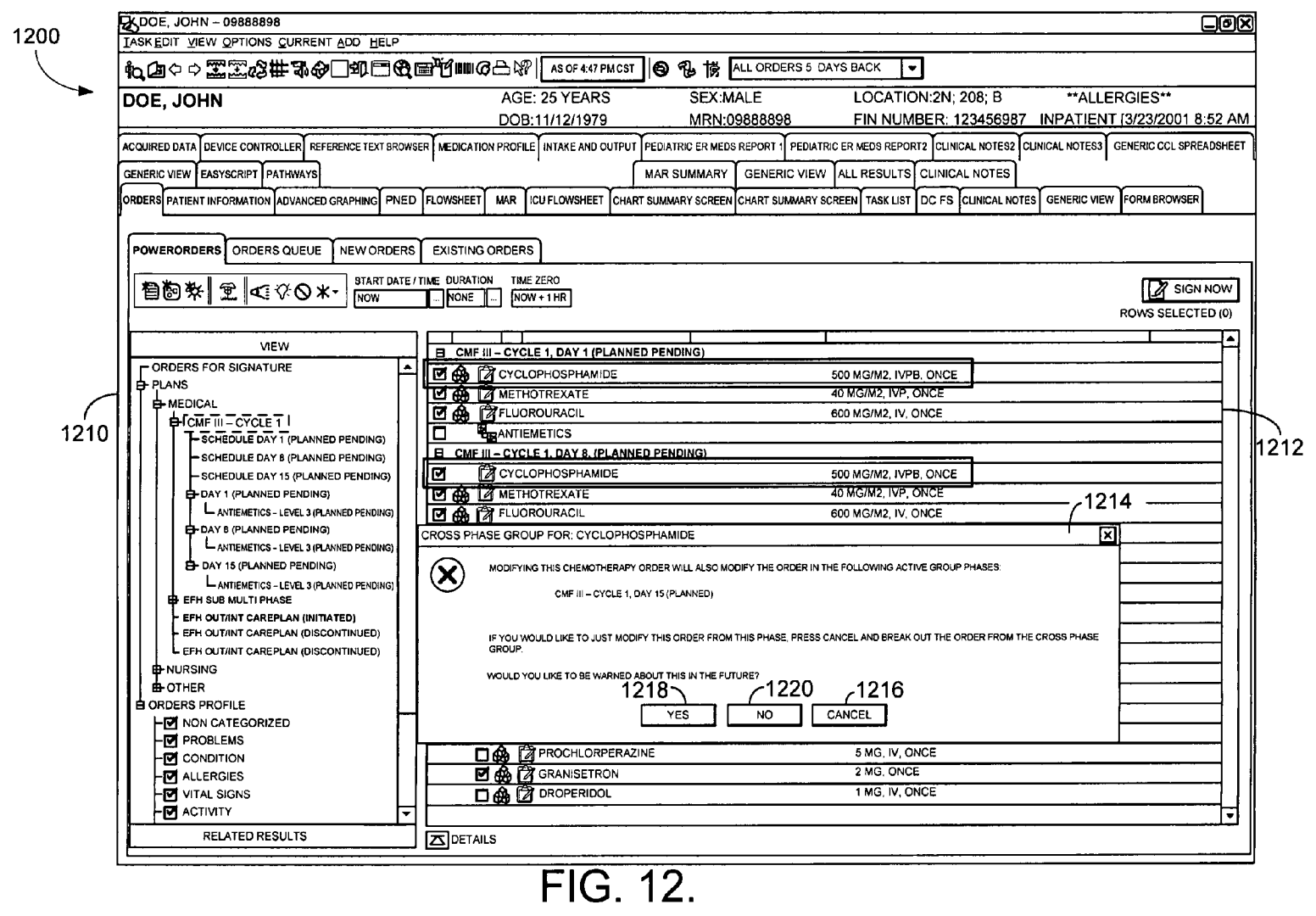
Figure 13:
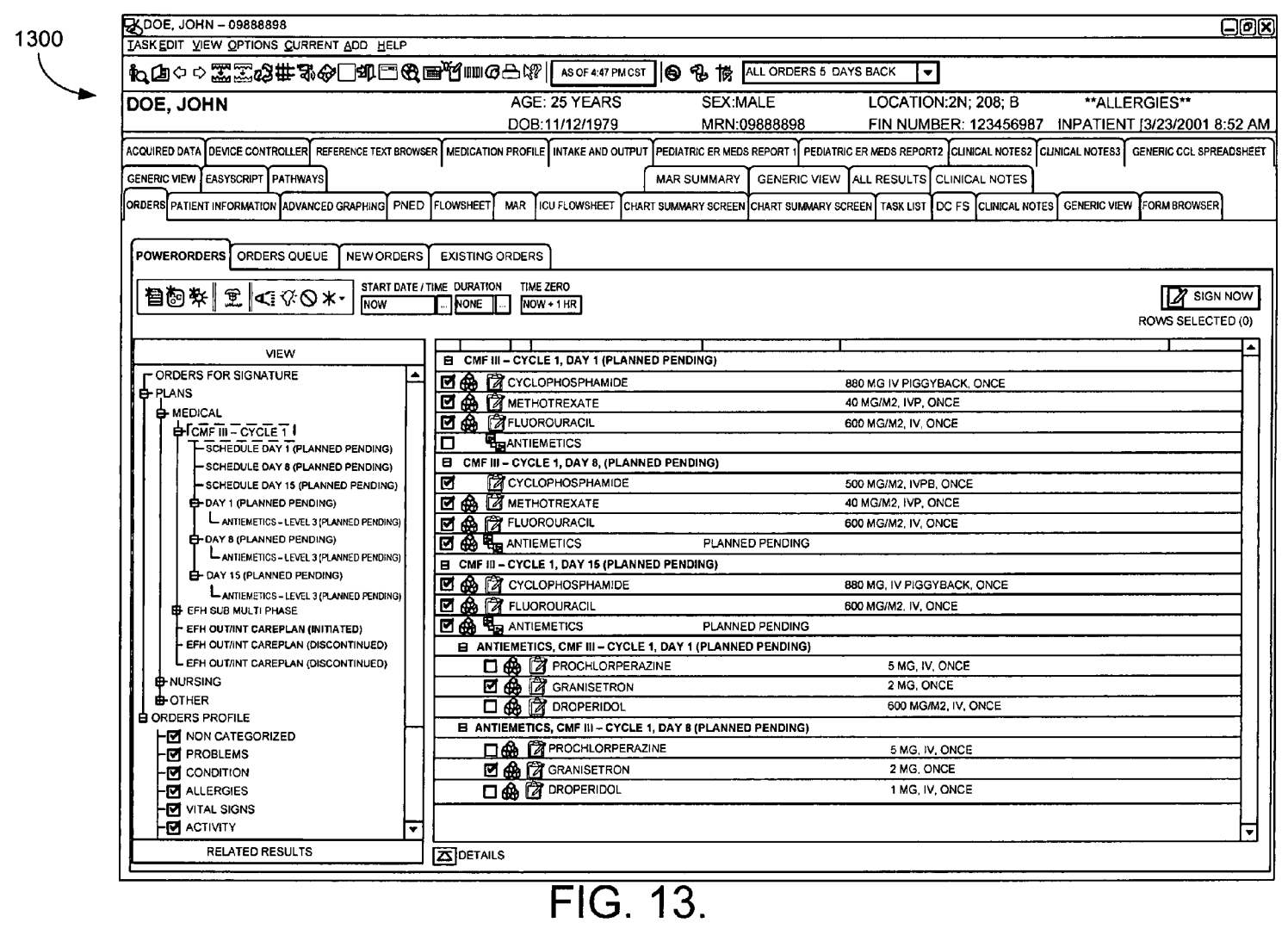

If it was determined at the step indicated by block 320 of FIG. 3 that the component for which modification was requested had been broken out of the cross-phase group, the dosage modification is applied only to the component in association with which the modification was made. If, however, it was determined at the step indicated by block 320 of FIG. 3 that the component for which modification was requested had not been broken out of the cross-phase group, the dosage modification is applied to all components which are members of the cross-phase group except for any components which have been broken out of the cross-phase group (or dithered). Exemplary screen displays in accordance with this latter embodiment are shown in FIGS. 12 and 13.

In one embodiment, if a modification is to be made for all components which are members of a cross-phase group (excepting those members which have been broken out of the group or dithered), an alert may be displayed to inform the user that the requested modification will be made to more than just the component with which the modification is directly associated. An exemplary alert is shown in FIG. 12. FIG. 12 shows a screen display 1200 of an exemplary view illustrating an alert that may be presented to a user upon attempting to modify a component which is a part of a cross-phase group, in accordance with an embodiment of the present invention. Screen display 1200 includes a navigation portion 1210, a phase details portion 1212, and a cross-phase group alert portion 1214. Screen display 1200 corresponds to the dosage modification which was implemented in screen display 1100 of FIG. 11.

Recall that in FIG. 11, the user had selected to modify the dosage of cyclophosphamide in association with Day 1 of the healthcare plan. Upon selection of the "apply dose" indicator 1118 of the attribute modification portion 1114 of the screen display 1100 of FIG. 11, the cross-phase group alert portion 1214 shown in the screen display 1200 of FIG. 12 may be displayed. The cross-phase group alert portion 1214 contains text informing the user that the requested dosage modification will be applied not only to the component with which its entry was associated but also to the other components that have not been broken out of the cross-phase group or dithered. In the illustrated embodiment, the only other component of the cyclophosphamide cross-phase group that had not been broken out of the group is the administration of cyclophosphamide to be administered on Day 15. (Recall that the administration of cyclophosphamide on Day 8 had been broken out of the group with reference to the screen displays shown in FIGS. 9A and 9B.)

If the user did not intend for the modification to be applied to any of the cross-phase group components other than the one with which entry of the modification was associated, s/he may select the cancel indicator 1216 to cancel the modification. Selection of either the "yes" indicator 1218 or the "no" indicator 1220, however, will cause the modification to be applied to all members of cross-phase group which have not been broken out of the group.

With reference to FIG. 13, a screen display of an exemplary view illustrating that the modification implemented in the screen display of FIG. 11 has been applied to all components of the cross-phase group except for those components which have been broken out of the group, in accordance with an embodiment of the present invention, is shown and designated generally as reference numeral 1300. Note that while the dosage associated with each of cyclophosphamide to be administered on Day 1 and cyclophosphamide to be administered on Day 15 has been modified (with reference to the screen display 1000 shown in FIG. 10) to an actual dosage of 880 mg, the dosage of cyclophosphamide to be administered on Day 8 has remained normalized at 500 mg/m$^2$.

Figure 14:
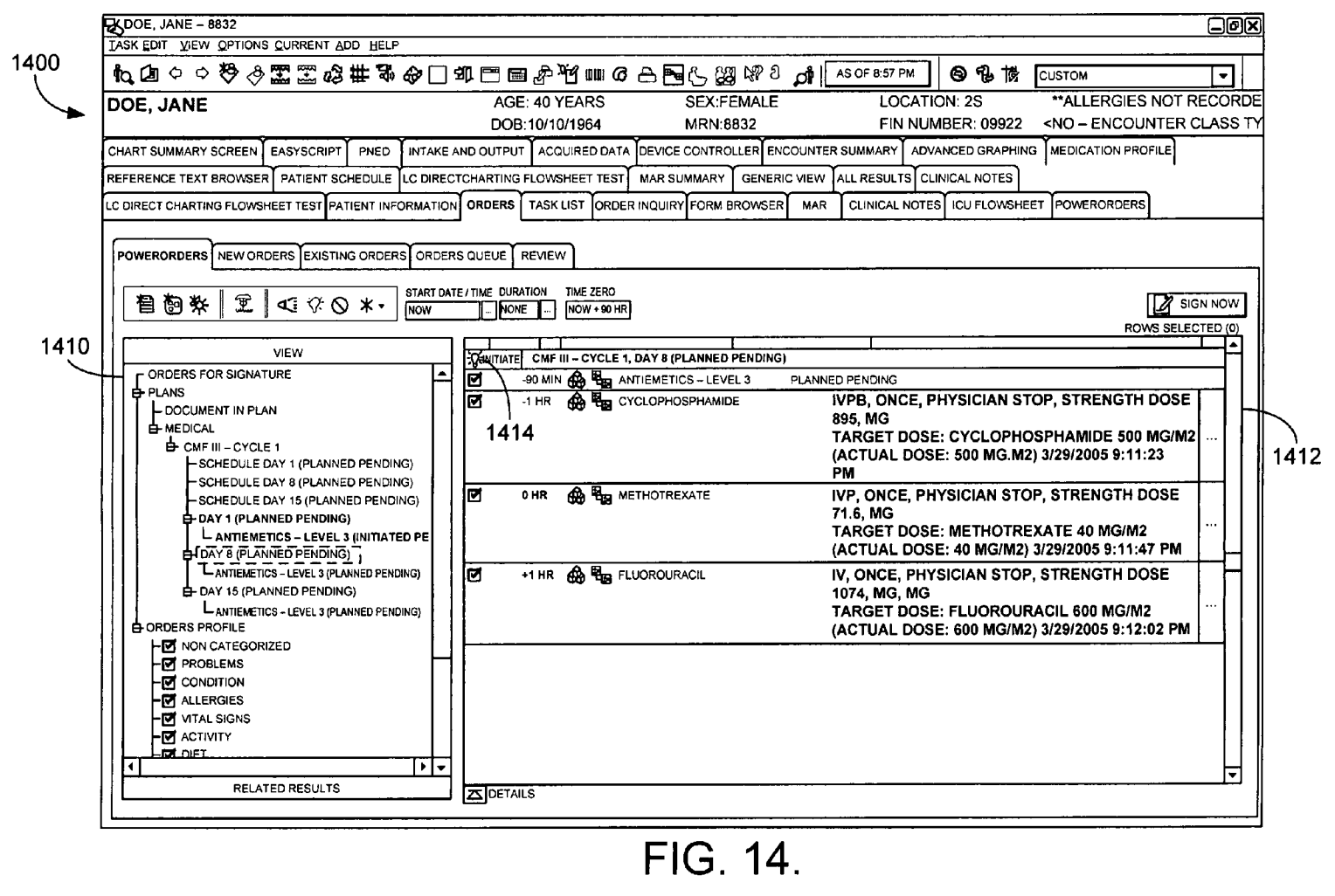

Once all modifications to a phase of a healthcare plan have been implemented, the phase must be initiated and signed prior to being carried out by the appropriate healthcare personnel. With reference to FIG. 14, a screen display of an exemplary view from which a particular phase of a cross-phase group may be initiated, in accordance with an embodiment of the present invention, is shown and designated generally as screen display 1400. Screen display 1400 includes a navigation portion 1410 and a phase details portion 1412. Screen display 1400 further includes an "initiate" indicator 1414. Note that the phase details portion 1412 of the screen display 1400 indicates that the phase is "planned pending". User selection of the "initiate" indicator initiates the phase. Upon such initiation, the "planned pending" indication in the phase details portion 1412 is changed to "initiated," as shown in FIG. 15.

Figure 15:
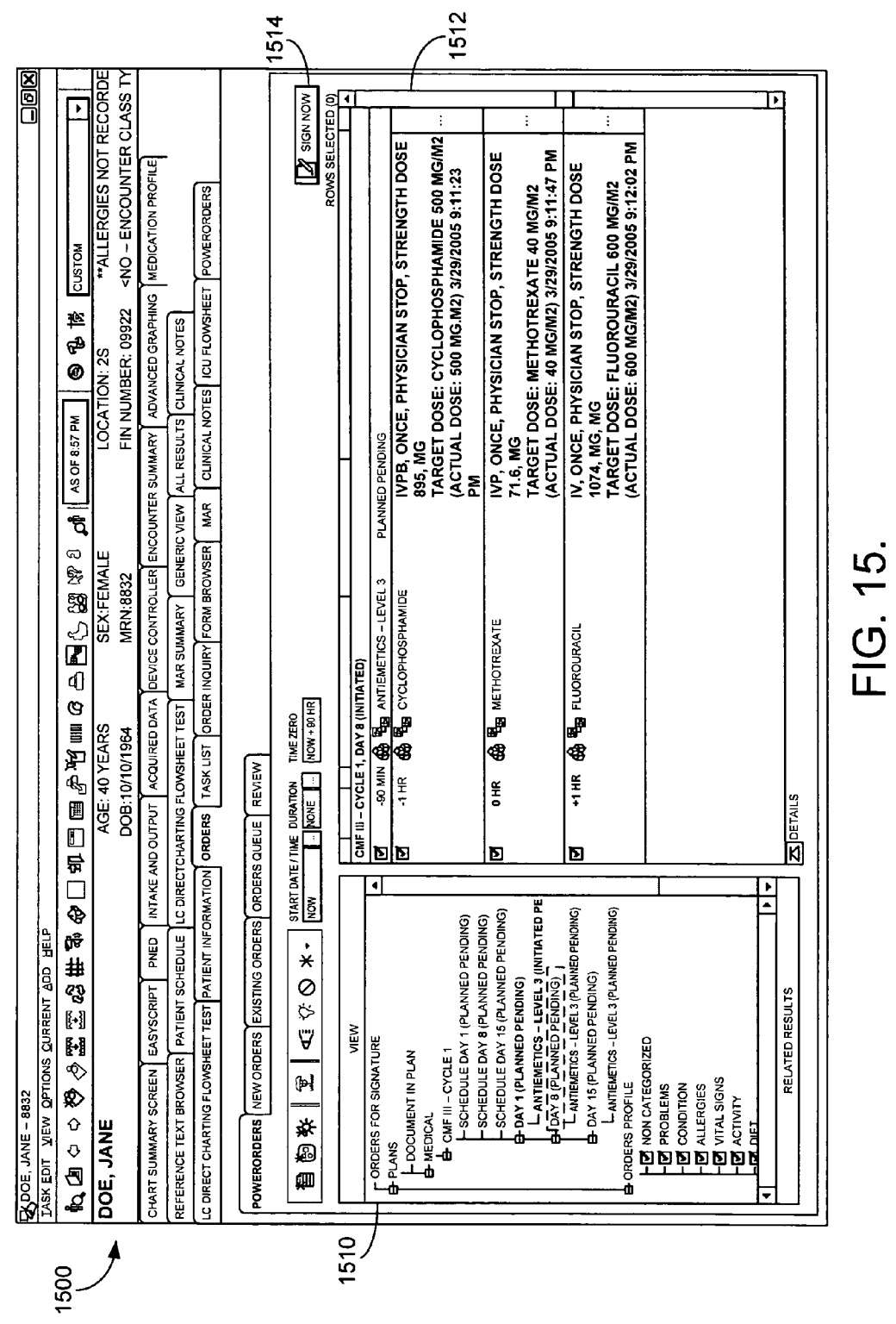

With reference to FIG. 15, a screen display of an exemplary view illustrating the particular phase of the cross-phase group has been initiated but still needs to be signed, in accordance with an embodiment of the present invention, is shown and designated generally as reference numeral 1500. Screen display 1500 includes a navigation portion 1510 and a phase details portion 1512. Screen display 1500 further includes a "sign now" indicator 1514. User selection of the "sign now" indicator permits the phase to be implemented as set forth in the phase details portion 1512. It will be understood and appreciated by those of ordinary skill in the art that a check of the authority of the user to initiate and/or sign the order(s) of the phase such that they may be implemented may be conducted prior to initiation and/or signing of such order(s). All such variations, and any combination thereof, are contemplated to be within the scope of embodiments of the present invention. Note that once signed, the components of the CMF III-Cycle 1, Day 8 order will become dithered and any modifications made to other components of the cross-phase group(s) of which the order components are part will not be applied to the CMF III-Cycle 1, Day 8 components.

Figure 4:
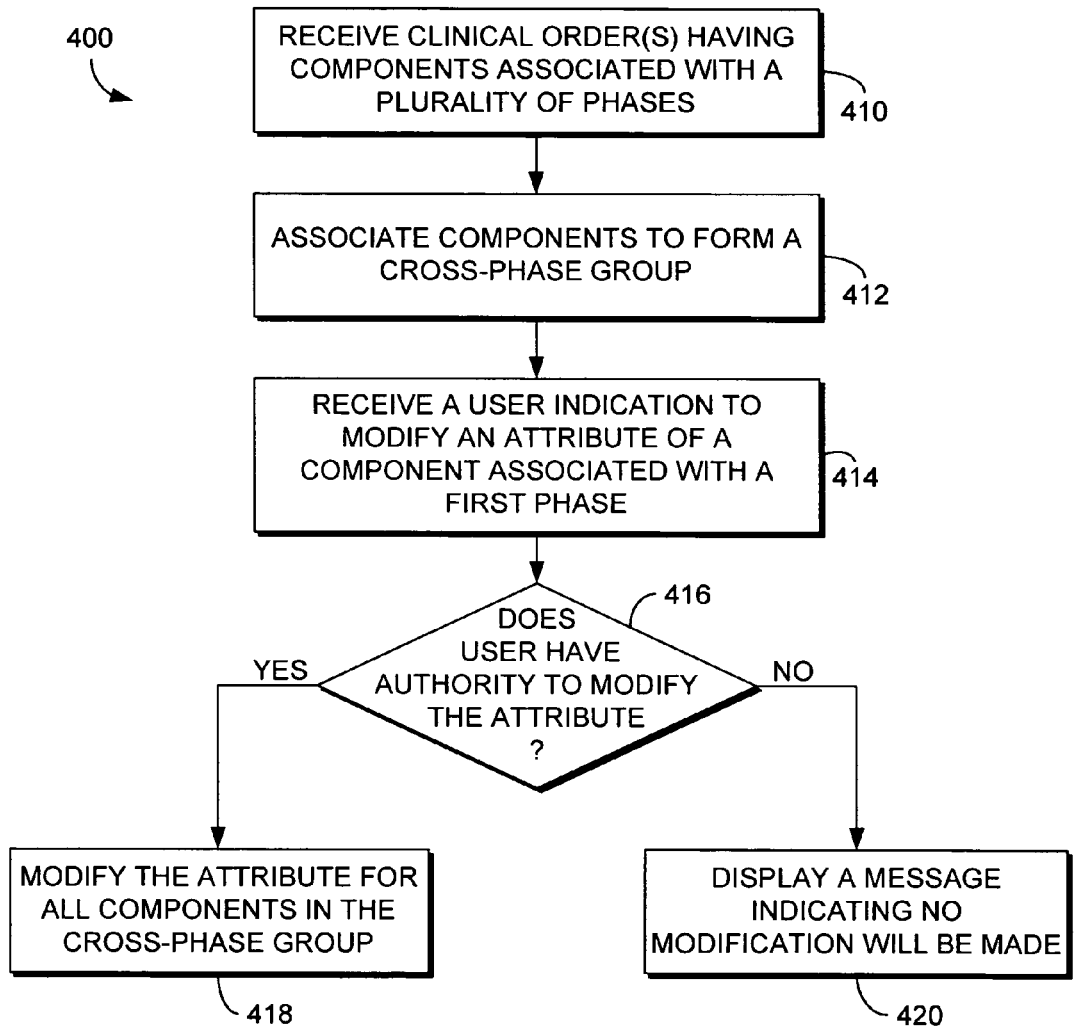
FIG. 4 is a flow diagram showing a method for modifying at least one component of a clinical order, wherein a plurality of components derived from the clinical order are associated to form a cross-phase group, and wherein the authority of an individual attempting to modify the at least one component is verified prior to any modification being implemented, in accordance with an embodiment of the present invention.

In another embodiment, the present invention relates to a method for modifying at least one component of a clinical order, wherein a plurality of components derived from the clinical order are associated to form a cross-phase group, and wherein the authority of an individual attempting to modify the at least one component is verified prior to any modification being implemented. With reference to FIG. 4, a flow diagram representative of such a method in accordance with an embodiment of the present invention is illustrated and depicted generally as reference numeral 400. As with methods 200 of FIG. 2 and 300 of FIG. 3, method 400 may be implemented in the above-described exemplary computing system environment (FIG. 1).

Initially, as shown at block 410, the system receives one or more clinical orders having components associated with a plurality of phases. For instance, contemplate that a healthcare plan containing a chemotherapy protocol for a patient specifies that the medication cyclophosphamide is to be administered to the patient in a normalized dose of 500 mg/m$^2$ on each of Day 1, Day 8, and Day 15 of treatment. In this instance, each of Day 1, Day 8, and Day 15 are different phases and cyclosphophamide is the component associated with each phase. Administration instructions for each phase may be included in three separate orders or may be included in a single order.

Next, as shown at block 412, the components (or some portion thereof) are associated with one another to form a cross-phase group. For instance, a first component associated with a first phase and a second component associated with a second phase may be associated with one another to form a cross-phase group. Association of the components with one another may be accomplished in a number of ways including, by way of example only, user selection for inclusion as illustrated in screen displays of FIGS. 5A-5C and discussed herein above.

Subsequently, the system receives a user indication to modify an attribute of a component associated with a first of the plurality of phases. This is indicated at block 414. Such indication may be received, for instance, if a clinician wishes to implement a modification one or more of the components associated to form the cross-phase group. One exemplary manner in which such indication may be received was discussed herein above with reference to FIG. 6. Another exemplary manner in which such indication may be received was discussed herein above with reference to FIG. 11.

Upon receiving such indication, the system determines whether or not the user attempting to make the modification has the authority to modify the attribute as requested. This is indicated at block 416. In one embodiment, If it is determined that the user does have the authority to modify the attribute as requested, the attribute is modified for all components in the cross-phase group, as indicated at block 418. If, however, it is determined that the user does not have the authority to modify the attribute as requested, the attempted modification is not made and the system displays a message to the user indicating that no modification will be made. This is indicated at block 420.

As can be understood, embodiments of the present invention provide computerized methods and systems for modifying at least one component of a clinical order. Embodiments of the present invention further provide computerized methods and systems for modifying at least one component of a clinical order, wherein a plurality of components derived from the clinical order are associated with one another to form a cross-phase group. Still further, embodiments of the present invention provide computerized methods and systems for modifying at least one component of a clinical order, wherein a plurality of components derived from the clinical order are associated to form a cross-phase group, and wherein at least one of the associated components has been broken out of the group.

The present invention has been described in relation to particular embodiments, which are intended in all respects to be illustrative rather than restrictive. Alternative embodiments will become apparent to those of ordinary skill in the art to which the present invention pertains without departing from its scope.

From the foregoing, it will be seen that this invention is one well adapted to attain all the ends and objects set forth above, together with other advantages which are obvious and inherent to the system and method. It will be understood that certain features and sub-combinations are of utility and may be employed without reference to other features and sub-combinations. This is contemplated by and within the scope of the claims.

What is claimed is:

1. A method in a clinical computing environment for verifying authority to modify at least one clinical order, the method comprising:
   receiving, through a first computing process, the at least one clinical order, the at least one clinical order having components that are administered in two or more phases, wherein a phase is a sub-plan within a healthcare plan, wherein individual phases are separated from other phases by at least one day; and wherein a healthcare plan includes multiple orders for the treatment of a particular ailment in a patient;
   associating, through a second computing process, a plurality of the components to form a cross-phase group, the plurality of the components including at least a component associated with a first phase and a component associated with a second phase, wherein each of the components in the cross-phase group includes a common attribute, wherein the common attribute is a clinical detail related to administration of the at least one clinical order to the patient, and wherein the first phase and the second phase occur at least one day apart;
   receiving, through a third computing process, a user indication to modify the common attribute of the component associated with the first phase; and
   determining, through a fourth computing process, whether a user from whom the user indication is received has the authority to modify the common attribute of the component associated with the first phase; and
   modifying, through a fifth computing process and in response to the user indication, the common attribute of all components in the cross-phase group in the same way, wherein the first, second, third, fourth, and fifth computing processes are performed on one or more computing devices.

2. The method of claim 1, further comprising displaying, through a sixth computing process, a message indicating that the common attribute of the component associated with the first phase will be modified in response to the indication received, wherein the sixth computing process is performed on the one or more computing devices.

3. The method of claim 1, wherein the first phase and the second phase are separated by a period of time greater than six days.

4. The method of claim 1, wherein the common attribute a route of administration for a medication.

5. The method of claim 3, wherein the common attribute is a medication dosage.

6. The method of claim 3, wherein the common attribute is an administration frequency for a medication.

7. A method in a clinical computing environment for verifying authority to modify at least one clinical order, the method comprising:
   receiving, through a first computing process, the at least one clinical order, the at least one clinical order having components associated with a plurality of phases, wherein a phase is one or more clinical orders occurring within a period of time;
   associating, through a second computing process, a plurality of the components to form a cross-phase group, the plurality of the components including at least a component associated with a first phase and a component associated with a second phase, wherein each of the components in the cross-phase group includes a common attribute, and wherein the first phase is separated by at least one day from the second phase;

receiving, through a third computing process, a user indication to modify the common attribute of the component associated with the first phase; and modifying, through a fourth computing process and in response to the user indication, the common attribute of all components in the cross-phase group, wherein the first, second, third, and fourth computing processes are performed on one or more computing devices.

8. The method of claim 7, further comprising determining, through a fifth computing process, whether a user from whom the user indication is received has the authority to modify the common attribute of the component associated with the first phase, wherein the fifth computing process is performed on the one or more computing devices.

9. The method of claim 7, wherein the first phase and the second phase are separated by a period of time greater than six days.

10. The method of claim 7, wherein the common attribute is a medication dosage.

11. The method of claim 7, wherein the common attribute a route of administration for a medication.

12. The method of claim 7, wherein the common attribute is an administration frequency for a medication.

13. The method of claim 8, further comprising a displaying, through a sixth computing process, a message indicating that the user from whom the user indication is received has the authority to modify the common attribute, wherein the sixth computing process is performed on the one or more computing devices.

14. One or more computer-readable media having computer-executable instructions embodied thereon that when executed by one or more computing devices perform a method for verifying authorization to modify at least one clinical order, the method comprising;

receiving, at the one or more computing devices, the at least one clinical order, the at least one clinical order having components associated with a plurality of phases, wherein a phase is a sub-plan within a healthcare plan, wherein individual phases are separated from other phases by at least one day, and wherein a healthcare plan includes multiple orders for the treatment of a particular ailment in a patient;

generating, at the one or more computing devices, a cross-phase group that includes at least two of the components, the at least two components including at least a component associated with a first phase and a component associated with a second phase, wherein each of the components in the cross-phase group includes a common attribute, and wherein the first phase and the second phase occur at least one day apart;

receiving, at the one or more computing devices, a user indication to modify the common attribute of the component associated with the first phase; and determining, at the one or more computing devices, whether a user from whom the user indication is received has the authority to modify the common attribute of the component associated with the first phase.

15. The media of claim 14, further comprising modifying, at the one or more computing devices, all components that are associated in the cross-phase group in response to the indication received if it is determined that the user from whom the user indication is received has the authority to modify the common attribute.

16. The media of claim 14, further comprising displaying, through a user interface coupled to the one or more computing devices, a message indicating that the common attribute will not be modified in response to the indication received if it is determined that the user from whom the user indication is received does not have the authority to modify the common attribute.

* * * * *